US010407662B2

(12) United States Patent
Murakami et al.

(10) Patent No.: US 10,407,662 B2
(45) Date of Patent: *Sep. 10, 2019

(54) METHOD OF CULTURING PLURIPOTENT STEM CELL, AND POLYPEPTIDE TO BE USED THEREFOR

(71) Applicant: FUJIFILM Corporation, Minato-ku, Tokyo (JP)

(72) Inventors: Yuta Murakami, Kanagawa (JP); Rie Iwata, Kanagawa (JP); Yoshihide Iwaki, Kanagawa (JP); Tasuku Sasaki, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 154 days.

This patent is subject to a terminal disclaimer.

(21) Appl. No.: 15/291,246

(22) Filed: Oct. 12, 2016

(65) Prior Publication Data
US 2017/0022473 A1    Jan. 26, 2017

Related U.S. Application Data

(63) Continuation of application No. 14/528,197, filed on Oct. 30, 2014, now abandoned, which is a continuation of application No. PCT/JP2013/062122, filed on Apr. 24, 2013.

(30) Foreign Application Priority Data

May 1, 2012   (JP) ................. 2012-104816

(51) Int. Cl.
| | |
|---|---|
| *C07K 14/78* | (2006.01) |
| *C12N 5/00* | (2006.01) |
| *C12N 5/074* | (2010.01) |
| *C07K 14/00* | (2006.01) |
| *C07K 14/47* | (2006.01) |
| *C12N 15/63* | (2006.01) |

(52) U.S. Cl.
CPC .......... *C12N 5/0068* (2013.01); *C07K 14/001* (2013.01); *C07K 14/47* (2013.01); *C07K 14/78* (2013.01); *C12N 5/0607* (2013.01); *C12N 5/0696* (2013.01); *C12N 2533/50* (2013.01); *C12N 2533/52* (2013.01); *C12N 2537/00* (2013.01)

(58) Field of Classification Search
CPC .. C12N 5/0068; C12N 5/0696; C12N 5/0607; C07K 14/001; C07K 14/78; C07K 14/47
See application file for complete search history.

(56) References Cited

U.S. PATENT DOCUMENTS

| 8,431,363 B2 | 4/2013 | Reed | |
|---|---|---|---|
| 9,938,505 B2 * | 4/2018 | Hagiya | ................... C07K 14/78 |
| 2005/0048057 A1 | 3/2005 | Day | |

FOREIGN PATENT DOCUMENTS

| JP | 2001-17183 A | 1/2001 |
|---|---|---|
| JP | 2010-29186 A | 2/2010 |
| JP | 2012-502664 A | 2/2012 |
| WO | 2004/023973 A2 | 3/2004 |
| WO | 2012/032169 A1 | 3/2012 |

OTHER PUBLICATIONS

Office Action dated Nov. 21, 2017 from the Canadian Patent Office in counterpart Canadian Application No. 2,872,467.
Andrew B.J. Prowse et al., "Long term culture of human embryonic stem cells on recombinant vitronectin in ascorbate free media", Biomaterials 2010, pp. 8281-8288, vol. 31.
Chillakuri et al, "Heparin binding domain in vitronectin is required for oligomerization and thus enhances integrin mediated cell adhesion and spreading," FEBS Letters, vol. 584, No. 15, Jun. 14, 2010, pp. 3287-3291, XP028340487.
Manton et al., "A Chimeric Vitronectin: IGF-I Protein Supports Feeder-Cell-Free and Serum-Free Culture of Human Embryonic Cells, Stem Cells and Development," vol. 19, No. 9, Sep. 1, 2010, pp. 1297-1305, XP055010532.
Notice of Reasons for Rejection, dated Sep. 15, 2015, issued in related JP Application No. 2014-513364, 5 pages in English and Japanese.
Chunhui Xu et al., "Feeder-free growth of human undifferentiated human embryonic stem cells", Nature Biotechnology, Oct. 2001, pp. 971-974, vol. 19.
Office Action dated Jan. 27, 2016, issued by the State Intellectual Property Office of the P.R.C. in corresponding Chinese Application No. 201380022493.2.
Communication, dated Oct. 20, 2015, issued in corresponding EP Application No. 13784603.6, 9 pages in English.
Guokai Chen et al., "Chemically defined conditions for human iPSC derivation and culture", Nature Methods, May 2011, pp. 424-429, vol. 8, No. 5.
International Search Report for PCT/JP20103/062122 dated May 21, 2013.
Klim et al., "A defined glycosaminoglycan-binding substratum for human pluripotent stem cells," Nature Methods, vol. 7, No. 12, Dec. 1, 2010, pp. 989-994, XP055061190.

(Continued)

*Primary Examiner* — Quang Nguyen
(74) *Attorney, Agent, or Firm* — Sughrue Mion, PLLC

(57) ABSTRACT

A polypeptide including: (1) a first region containing at least one selected from the group consisting of an amino acid sequence represented by CSYYQSC (SEQ ID NO:1) and an amino acid sequence represented by RGD; and (2) a second region containing (2-i) an amino acid sequence represented by PRPSLAKKQRFRHRNRKGYRSQRGHSRGRNQN (SEQ ID NO:2), (2-ii) an amino acid sequence having an identity of not less than 50% to the amino acid sequence represented by SEQ ID NO:2 and having an adsorption ability to a cultivation container, or (2-iii) an amino acid sequence that is the amino acid sequence represented by SEQ ID NO:2 in which from 1 to 30 amino acid residues are added, substituted, or deleted, and has an adsorption ability to a cultivation container, in which the polypeptide includes from 40 to 450 amino acid residues.

4 Claims, 4 Drawing Sheets

Specification includes a Sequence Listing.

(56) References Cited

OTHER PUBLICATIONS

Office Action, dated Nov. 10, 2015, issued in related Canadian Application No. 2,872,467, 4 pages in English.
Schleicher et al., "Surface Modification by Complexes of Vitronectin and Growth Factors for Serum-Free Culture of Human Osteoblasts," Tissue Engineering, vol. 11, No. 11-12, Nov. 1, 2005, pp. 1688-1698, XP009072079.
Written Opinion for PCT/JP20103/062122 dated May 21, 2013.
Zara Melkoumian et al., "Synthetic peptide-acrylate surfaces for long-term self-renewal and cardiomyocyte differentiation of human embryonic stem cells", Nature Biotechnology, Jun. 1010, p. 606-612, vol. 28, No. 6.
Horn et al., J. Biol. Chem 2004; 279:35867-78.
Bowie et al., Science Mar. 1990; 247:1306-10.
Ngo, In the Protein Folding Problem and Tertiary Structure Predictiion, Merz et al (eds.), Birkhauser Boston: Boston, MA, pp. 433 and 492-495, 1994.
Rudinger, in Peptide Hormones, Parsons (ed.), University Park Press: Baltimore, MD pp. 1-7, 1976.
Office Action dated Nov. 23, 2016 from the European Patent Office in counterpart European Patent Application No. 13784603.6.
Office Action dated Oct. 18, 2016 from the Canadian Intellectual Property Office in counterpart Canadian Application No. 2,872,467.

\* cited by examiner

METHOD OF CULTURING PLURIPOTENT STEM CELL, AND POLYPEPTIDE TO BE USED THEREFOR

CROSS-REFERENCE TO RELATED APPLICATIONS

This is a continuation of U.S. application Ser. No. 14/528,197 filed Oct. 30, 2014, which is a continuation of International Application No. PCT/JP2013/062122 filed Apr. 24, 2013, which claims priority from Japanese Patent Application No. 2012-104816 filed May 1, 2012. All of these prior applications are incorporated herein by reference.

TECHNICAL FIELD

The present invention relates to a method of culturing a pluripotent stem cell and to a polypeptide to be used in the method.

BACKGROUND

Various kinds of regenerative medicine have been developed for the purpose of the functional recovery of damaged tissues and the like. Especially, many technologies for primate, particularly human totipotent or pluripotent stem cells, of which the ultimate goal have been the regeneration of tissues per se, and the like, have been reported. Unlike embryonic stem cells, induced pluripotent stem cells (iPS cells) particularly have had an advantage that the induced pluripotent stem cells are less ethically problematic because the induced pluripotent stem cells are induced from somatic cells.

In a case of culturing primate totipotent or pluripotent stem cells (both cells are generically simply referred to as "pluripotent stem cell" in the invention), it is required to maintain the primate totipotent or pluripotent stem cells in an undifferentiated state for a long term. In order to culture the pluripotent stem cells in an undifferentiated state for a long term, feeder cells such as mouse fibroblasts are generally used.

However, it has been pointed out that the use of the feeder cells derived from heterologous animals, such as the mouse fibroblasts, cause contamination of culture liquids with foreign substances such as antigenic substances derived from heterologous animals. In a case in which totipotent or pluripotent stem cells are used in medical applications or applications equivalent thereto, it has been demanded that the cells are cultured in the absence of the feeder cells.

In view of such circumstances, cell-adhesive materials of which the functions substitute for those of feeder cells have been developed. For example, it is disclosed in Nature Biotechnology, 2001, Vol. 19, pp. 971-974 that human embryonic stem cells maintained in an undifferentiated state are successfully cultured using, as a substitute for feeder cells, Matrigel, which is a component extracted from mouse sarcoma.

In Japanese Patent Application Laid-Open (JP-A) No. 2001-17183, a cellular composition that does not contain any feeder cells but contains proliferating primate progenitor cells is disclosed, and the cellular composition that further contains an extracellular matrix is disclosed as a preferred embodiment. In Japanese Patent Application Laid-Open (JP-A) No. 2010-29186, a cell culture matrix in which a cell culture surface subjected to plasma polymerization is further coated with a coating solution containing a predetermined concentration of extracellular matrix protein and an aqueous solvent is disclosed, and it is described that the cell culture matrix has favorable adhesiveness helpful for avoiding the differentiation of embryonic stem cells. In Japanese National-Phase Publication (JP-A) No. 2012-502664, a peptide that binds to a glycosaminoglycan (GAG) is disclosed.

In Biomaterials, 2010, November; Vol. 31 (32), pp. 8281-8288 and Nature Biotechnology, 2010, Vol. 28, No. 6, pp. 606-610, recombinant or synthetic peptides containing a vitronectin partial sequence that can contribute to the long-term culture of embryonic stem cells, specifically, each of the sequence of 1st to the 52nd amino acids of natural vitronectin (see Biomaterials, 2010, November; Vol. 31(32), pp. 8281-8288) and the sequence of the 41st to 52nd amino acids containing an RGD sequence (Nature Biotechnology, 2010, Vol. 28, No. 6, pp. 606-610) are disclosed, The peptides have been known to be excellent in view of the fact that: the possibility of contamination with antigenic substances and the like can be avoided since the peptides are non-biological samples; and the peptides can be industrially produced.

SUMMARY OF INVENTION

Technical Problem

However, uses of heterologous feeder cells such as fibroblasts derived from mice and the like, and components derived from heterologous animals, including Matrigel derived from mice, should be avoided as much as possible, considering that pluripotent stem cells are used in medical applications such as regenerative medicine or applications equivalent thereto. Even in a case of a cell or a component derived from a homologous animal, it is impossible to completely eliminate the possibility of the contamination of the cell or the component with an antigenic substance or the like. Any homologous or heterologous material derived from a living body is not preferred even from an industrial viewpoint that, for example, the amount of the extracted material is an extremely minute amount, or the feature of the material may vary depending on a donor. In recent years, the culture of stem cells, aimed at being applied to medical applications, under a chemically identified condition, in which a component or an antigenic substance derived from a heterologous animal is not contaminated, has been examined vigorously. However, a material that can substitute for feeder cells exhibiting a cell culture feature sufficient for practical applications has not been found.

For example, an example of culturing embryonic stem cells for a long term using recombinant or synthetic peptides containing a partial sequence of human vitronectin is disclosed as a technique for avoiding the use of a material per se derived from a living body in Biomaterials, 2010, November; Vol. 31 (32), pp. 8281-8288 and Nature Biotechnology, 2010, Vol. 28, No. 6, pp. 606-610.

However, since such peptides have low adsorption to a cultivation container without discrimination, a step of chemically binding the peptides to the cultivation container is required. For example, an introduction of an acrylate into a cell culture surface in a cultivation container to covalently bind peptides is disclosed in Nature Biotechnology, 2010, Vol. 28, No. 6, pp, 606-610, However, this method has poor general-purpose properties and simpleness since it is impossible to freely select the culture surface to which the peptides are bound, and only the peptides are not sufficient for a cell culture feature for culturing embryonic stem cells (ESCs) and induced pluripotent stem cells (iPS). In JP-A No. 2012-502664, an isolated peptide binding to a glycosaminoglycan (GAG) is disclosed, and it is described that the peptide is used in the long-term culture and maintenance of ESCs and iPS utilizing a site binding to the glycosaminoglycan. However, only the binding site to the GAG is not sufficient for a cell culture feature for culturing ESCs and iPS.

Accordingly, an object of the invention is to provide a polypeptide that enables a pluripotent stem cell to proliferate in an undifferentiated state, does not require treatment of immobilization thereof to a cultivation container by chemical bonding, and can be industrially produced, and to provide a method of culturing a pluripotent stem cell using the polypeptide.

Solution to Problem

The present inventors repeated extensive research in order to develop a recombinant protein that enables pluripotent stem cells to proliferate in an undifferentiated state, has excellent adsorptivity to a cultivation container, and does not require treatment of immobilization to a cultivation container by chemical bonding, and found that a specific polypeptide that comprises an amino acid residue containing a specific human vitronectin N-terminal partial sequence and having an adsorption ability to a cultivation container enables pluripotent stem cells to proliferate in a culture liquid that does not contain any component derived from a heterologous animal while maintaining an undifferentiated state for a long term, and is adsorbed to a cultivation container without chemical bonding. It was further surprisingly found that the polypeptide consisting of the sequence has significantly excellent proliferation properties, compared to recombinant vitronectin consisting of a human vitronectin full-length sequence, and the invention was thus accomplished.

The invention provides the following embodiments:

[1] A polypeptide consisting of from 40 to 450 amino acid residues and comprising:
(1) a first region comprising at least one selected from the group consisting of an amino acid sequence represented by CSYYQSC (SEQ ID NO:1) and an amino acid sequence represented by RGD; and
(2) a second region comprising
(2-i) an amino acid sequence represented by PRPSLAKKQRFRHRNRKGYRSQRGHSRGRNQN (SEQ ID NO:2),
(2-ii) an amino acid sequence having an identity of not less than 50% to an amino acid sequence represented by SEQ ED NO:2 and having an adsorption ability to a cultivation container, or
(2-iii) an amino acid sequence that is the amino acid sequence represented by SEQ ID NO:2, in which from 1 to 30 amino acid residues are added, substituted, or deleted, and that has an adsorption ability to a cultivation container.

[2] The polypeptide according to [1], wherein a GRAVY value is from −2.0 to −0.95.

[3] The polypeptide according to [1] or [2], wherein the first region comprises both of the amino acid sequence represented by CSYYQSC (SEQ ID NO:1) and the amino acid sequence represented by RGD.

[4] The polypeptide according to any one of [1] to [3], wherein the polypeptide consists of from 40 to 400 amino acid residues.

[5] T The polypeptide according to any one of [1] to [4], further comprising a third region consisting of any one amino acid sequence of the following (3-i) to (3-iii):

(3-i) an amino acid sequence consisting of the 56th to 341st amino acid residues in an amino acid sequence represented by SEQ ID NO:3, or a partial amino acid sequence thereof,
(3-ii) an amino acid sequence having an identity of not less than 50% to the (3-i) amino acid sequence or partial amino acid sequence thereof; or
(3-iii) an amino acid sequence that is the (3-i) amino acid sequence or partial amino acid sequence thereof in which from 1 to 30 amino acid residues are added, substituted, or deleted.

[6] The polypeptide according to any one of [1] to [4], further comprising a third. region consisting of any one amino acid sequence of the following (3a-i) to (3a-iii):

(3a-i) an amino acid sequence consisting of the 132th to 341st amino acid residues in an amino acid sequence represented by SEQ ID NO:3, or a partial amino acid sequence thereof;
(3a-ii) an amino acid sequence having an identity of not less than 50% to the (3a-i) amino acid sequence or partial amino acid sequence thereof; or
(3a-iii) an amino acid sequence that is the (3a-i) amino acid sequence or partial amino acid sequence thereof in which from 1 to 30 amino acid residues are added, substituted, or deleted.

[7] The polypeptide according to any one of [1] to [4], further comprising a third region consisting of any one amino acid sequence of the following (3b-i) to (3b-iii):

(3b-i) an amino acid sequence consisting of the 269th to 341st amino acid residues in an amino acid sequence represented by SEQ ID NO:3, or a partial amino acid sequence thereof;
(3b-ii) an amino acid sequence having an identity of not less than 50% to the (3b-i) amino acid sequence or partial amino acid sequence thereof; or
(3b-iii) an amino acid sequence that is the (3b-i) amino acid sequence or partial amino acid sequence thereof in which from 1 to 30 amino acid residues are added, substituted, or deleted.

[8] The polypeptide according to any one of [1] to [7], further comprising a fourth region consisting of any one amino acid sequence of the following (4-i) to (4-iii):

(4-i) an amino acid sequence consisting of the 374th to 459th amino acid residues in an amino acid sequence represented by SEQ ID NO:3, or a partial amino acid sequence thereof;
(4-ii) an amino acid sequence having an identity of not less than 50% to the (4-i) amino acid sequence or partial amino acid sequence thereof; or
(4-iii) an amino acid sequence that is the (4-i) amino acid sequence or partial amino acid sequence thereof in which from 1 to 30 amino acid residues are added, substituted, or deleted.

[9] The polypeptide according to any one of [1] to [8], wherein the (2-ii) amino acid sequence has an identity of not less than 80% to the amino acid sequence represented by SEQ ID NO:2.

[10] The polypeptide according to any one of [1] to [8], wherein the (2-iii) amino acid sequence is the amino acid sequence represented by SEQ ID NO:2 in which from 1 to 15 amino acid residues are added, substitute, or deleted.

[11] A polypeptide consisting of from 80 to 450 amino acid residues and comprising:
(1) a first region consisting of an amino acid sequence consisting of the 25th to 47th amino acid residues in an amino acid sequence represented by SEQ ID NO:3;

(2) a second region consisting of an amino acid sequence consisting of the 342nd to 373rd amino acid residues in the amino acid sequence represented by SEQ ID NO:3; and at least one selected from the group consisting of the following third and fourth regions:
(3) the third region consisting of an amino acid sequence consisting of the 269th to 341st amino acid residues in the amino acid sequence represented by SEQ ID NO:3, or a partial amino acid sequence thereof; and
(4) the fourth region consisting of an amino acid sequence consisting of the 374th to 459th amino acid residues in the amino acid sequence represented by SEQ ID NO:3, or a partial amino acid sequence thereof.

[12] A polypeptide consisting of from 100 to 450 amino acid residues and comprising:
(1) a first region consisting of an amino acid sequence consisting of the 1st to 55th amino acid residues in an amino acid sequence represented by SEQ ID NO:3;
(2) a second region consisting of an amino acid sequence consisting of the 342nd to 373rd amino acid residues in the amino acid sequence represented by SEQ ID NO:3; and at least one selected from the group consisting of the following third and fourth regions:
(3) the third region consisting of an amino acid sequence consisting of the 269th to 341st amino acid residues in the amino acid sequence represented by SEQ ID NO:3, or a partial amino acid sequence thereof; and
(4) the fourth region consisting of an amino acid sequence consisting of the 374th to 459th amino acid residues in the amino acid sequence represented by SEQ NO:3, or a partial amino acid sequence thereof.

[13] The polypeptide according to [11] or [12], wherein the polypeptide has a GRAVY value of from −2.0 to −0.95.

[14] The polypeptide according to any one of [1] to [13], the number of amino acid residues of which being 250 or less.

[15] The polypeptide according to any one of [5] to [14], wherein the polypeptide comprises the third region, and the third region comprises an amino acid residue other than a cysteine residue at a position corresponding to a cysteine residue in the amino acid sequence represented by SEQ ID NO:3.

[16] The polypeptide according to any one of [5] to [14], wherein the polypeptide comprises the third region, and the third region comprises a serine residue, an alanine residue, or a glycine residue at a position corresponding to a cysteine residue in the amino acid sequence represented by SEQ ID NO:3.

[17] The polypeptide according to any one of [1] to [16], wherein the first region is located at an N-terminal side of the second region.

[18] The polypeptide according to any one of [1] to [17], wherein two cysteine residues in the amino acid sequence represented by SEQ ID NO:1 are cross-linked to each other.

[19] A polypeptide comprising an amino acid sequence represented by any of SEQ ID NO:4 to SEQ ID NO:23, SEQ ID NO:38, or SEQ ID NO:39.

[20] A polypeptide, comprising an amino acid sequence represented by CSYYQSC (SEQ ID NO:1), and consisting of from 40 to 450 amino acid residues that have an adsorption ability to a cultivation container.

[21] The polypeptide according to [20], further comprising an amino acid sequence represented by RGD.

[22] The polypeptide according to [20] or [21], wherein the polypeptide has a GRAVY value of from −2.0 to −0.95.

[23] A method of culturing a pluripotent stem cell, comprising:

applying the polypeptide according to any one of [1] to [22] to a cell culture surface of a support, to obtain a polypeptide-coated culture surface; and seeding a pluripotent stem cell on the polypeptide-coated culture surface and culturing the pluripotent stem cell.

[24] The method of culturing a pluripotent stem cell according to [23], wherein the pluripotent stem cell is at least one selected from the group consisting of embryonic stem cells, induced pluripotent stem cells, somatic stem cells, fertilized egg inner cell mass cells, and early embryonic cells.

[25] The method of culturing a pluripotent stem cell according to [23] or [24], wherein the pluripotent stem cell is an induced pluripotent stem cell.

[26] The method of culturing a pluripotent stem cell according to any one of [23] to [25], wherein the pluripotent stem cell is cultured in the absence of a component derived from a heterologous animal and a component derived from serum.

[27] The method of culturing a pluripotent stem cell according to any one of [23] to [26], wherein an amount of application of the polypeptide to the cell culture surface is from 1 pmol/cm$^2$ to 1000 pmol/cm$^2$.

[28] A cultivation container comprising: a support comprising a cell culture surface; and the polypeptide according to any one of [1] to [22], placed on the cell culture surface of the support.

Effects of Invention

According to the invention, a polypeptide that enables a pluripotent stem cell to proliferate in an undifferentiated state, does not require treatment of immobilization to a cultivation container by chemical bonding, and can be industrially produced, and a method of culturing a pluripotent stem cell using the polypeptide can be provided.

DESCRIPTION OF EMBODIMENTS

Figure 1:
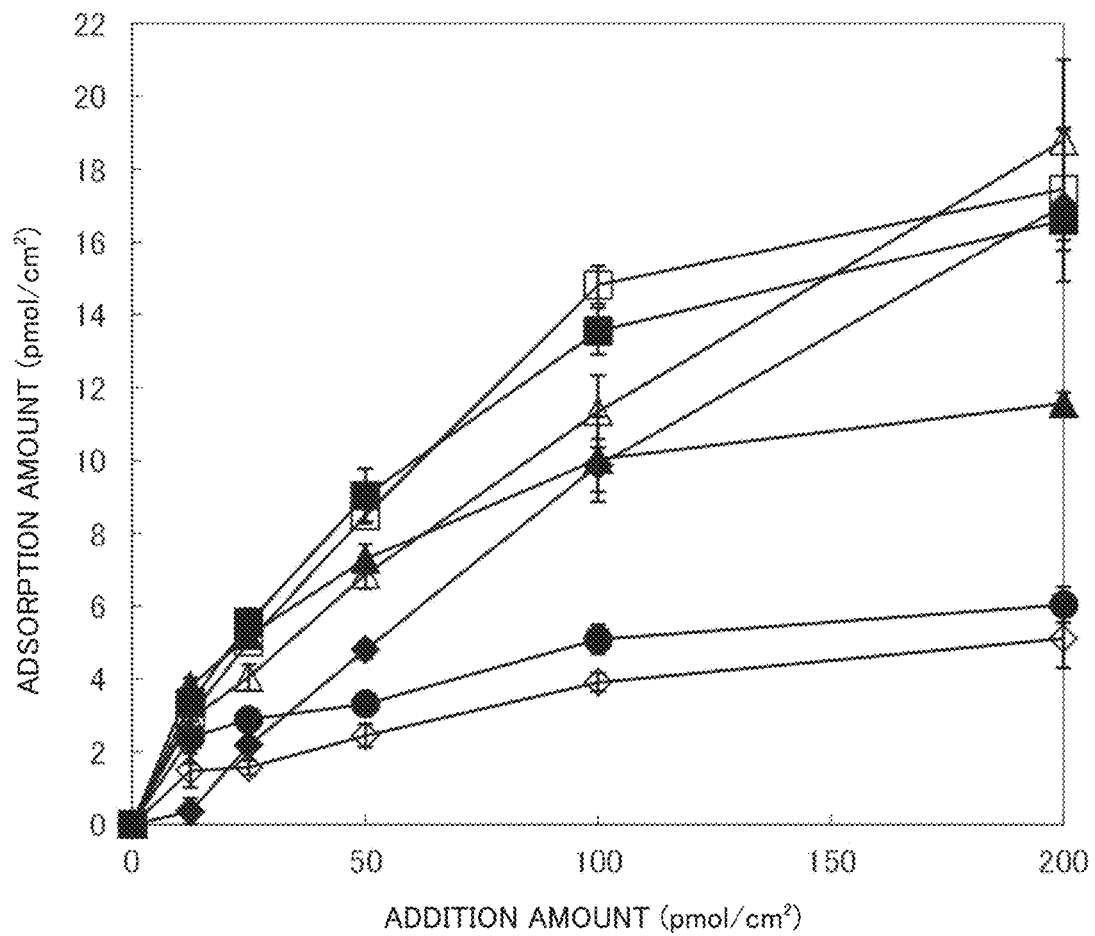
FIG. 1 is a graph indicating the results of the adsorption test of each polypeptide to the surface of a culture plate in Examples of the invention.

The polypeptide of the invention is: a polypeptide including (1) an amino acid sequence represented by CSYYQSC (SEQ ID NO:1), and consisting of from 40 to 450 amino acid residues that have an adsorption ability to a cultivation container; or a polypeptide consisting of from 40 to 450 amino acid residues and including: (1) a first region including at least one selected from the group consisting of an amino acid sequence represented by CSYYQSC (SEQ ID NO:1) and an amino acid sequence represented by RGD, and (2) a second region including (2-i) an amino acid sequence represented by PRPSLAKKQRFRHRNRKGYR-SQRGHSRGRNQN (SEQ ID NO:2), (2-ii) an amino acid sequence having an identity of not less than 50% to an amino acid sequence represented by SEQ ID NO:2 and having an adsorption ability to a cultivation container, or (2-iii) an amino acid sequence that is the amino acid sequence represented by SEQ ID NO:2, in which from 1 to 30 amino acid residues are added, substituted, or deleted, and that has an adsorption ability to a cultivation container. Hereinafter, the polypeptides may also be referred to as "polypeptides for use in culture" in the present specification. Note that the polypeptides may also be used for purposes other than use in culture.

It was found in the invention that the polypeptide for use in culture according to the invention enables cells, particularly pluripotent stem cells, to favorably proliferate since the first region containing a specific amino acid sequence has excellent cell adhesiveness. The polypeptide of the invention having such an amino acid sequence enables pluripotent stem cells to proliferate in a long term while maintaining an undifferentiated state.

It was further found in the invention that the second region containing a specific sequence contributes to adsorption to a surface of a cultivation container. The polypeptide of the invention having such an amino acid sequence exhibits favorable adhesiveness to a cultivation container, and an incorporation thereof in combination with the first region into the polypeptide enables pluripotent stem cells to proliferate in a long term while maintaining an undifferentiated state without separating from a cell culture surface of the cultivation container during a culture period. Further, since the polypeptide of the invention enables pluripotent stem cells in an undifferentiated state on culture to proliferate while being suppressed from separating from the surface of the cultivation container, and can improve handleability in a culture manipulation.

As a result, according to the invention, the polypeptide that promotes proliferation of pluripotent stem cells in an undifferentiated state, does not require treatment of immobilization to a cultivation container by chemical bonding, and can be industrially produced can be obtained.

The polypeptide according to the invention can eliminate the risk of contamination of an antigenic substance and an infection source compared to natural human vitronectin, and can retain features equivalent to those of natural vitronectin, i.e., adhesiveness to a pluripotent stem cell, cell proliferation properties, and undifferentiation maintenance properties.

The possibility of contamination of pluripotent stem cells cultured in a presence of the polypeptide according to the invention (preferably, further in the absence of a component derived from a heterologous animal or the like) with a foreign substance such as an antigenic substance derived from a sample or the like can be almost fully, or greatly eliminated. Safety of the pluripotent stem cells cultured in the culturing method can be sufficiently secured for use in medical applications or applications equivalent thereto.

The culturing method using the polypeptide of the invention enables pluripotent stem cells to be cultured at a lower cost and in a simple manipulation, and can widely contribute to demands not only in medical applications but also in research fields.

The term "step" as used herein encompasses not only an independent step but also a step that cannot be clearly distinguished from other steps, as long as the predetermined action of this step is achieved thereby.

In addition, a numerical value range expressed by "from (a minimum value) to (a maximum value)" represents a range which includes the values shown before and after the to as the minimum and maximum values, respectively.

In the case of mentioning of an amount of a certain component in a composition, in a case in which plural substances corresponding to the component are present in a composition, the amount means the total amount of the plural substances present in the composition, unless otherwise specified.

As used herein, the term "homologous" means a human while the term "heterologous" means an animal other than humans.

In the present specification, an amino acid residue in an amino acid sequence may be described in one character (for example, a glycine residue in "G") or three characters (for example, a glycine residue in "Gly"), well known in the art.

Unless otherwise specified, in the invention, "%" for amino acid sequences in polypeptides is based on the number of amino acid (or imino acid) residues.

In a case in which two or more amino acid sequences to be compared are aligned (alignment) in a manner well known in the art in a manner that the same amino acid residues are most in consideration of insertion, deletion, and substitution, the expression "corresponding amino acid residue" or the like used for a particular amino acid residue in one amino acid sequence, as used herein, means an amino acid residue in the other amino acid sequences, which matches with the position of the particular amino acid residue in the one amino acid sequence as a reference.

As used herein, "identity" related to an amino acid sequence can refer to a value calculated using the BLAST package (see Ausubel et al., 1999 Short Protocols in Molecular Biology, 4th Ed—Chapter 18), For example, an identity of not less than 50% to SEQ ID NO:2 refers to a value of Max. Identities in BLAST of 50 or more.

As used herein, vitronectin means human vitronectin, and specifically, is a polypeptide composed of 495 amino acid residues in full length, shown in SEQ ID NO:3 described below. It has also been confirmed that natural vitronectin is a glycoprotein having a sugar chain in a part of the sequence thereof.

```
SEQ ID NO: 3:
DQESCKGRCTEGFNVDKKCQCDELCSYYQSCCTDYTAECKPQVTRGDVF

TMPEDEYTVYDDGEEKNNATVHEQVGGPSLTSDLQAQSKGNPEQTPVLK

PEEEAPAPEVGASKPEGIDSRPETLHPGRPQPPAEEELCSGKPFDAFTD

LKNGSLFAFRGQYCYELDEKAVRPGYPKLIRDVWGIEGPIDAAFTRINC

QGKTYLFKGSQYWRFEDGVLDPDYPRNISDGFDGIPDNVDAALALPAHS

YSGRERVYFFKGKQYWEYQFQHQPSQEECEGSSLSAVFEHFAMMQRDSW

EDIFELLFWGRTSAGTRQPQFISRDWHGVPGQVDAAMAGRIYISGMAPR

PSLAKKQRFRHRNRKGYRSQRGHSRGRNQNSRRPSRATWLSLFSSEESN

LGANNYDDYRMDWLVPATCEPIQSVFFFSGDKYYRVNLRTRRVDTVDPP

YPRSIAQYWLGCPAPGHL
```

<Polypeptide>

The polypeptide according to the invention (polypeptide for use in culture) is: a polypeptide including an amino acid sequence represented by CSYYQSC (SEQ ID NO:1), and consisting of from 40 to 450 amino acid residues that have an adsorption ability to a cultivation container; or a polypeptide including the following first and second regions and consisting of from 40 to 450 amino acid residues:

(1) a first region including at least one selected from the group consisting of an amino acid sequence represented by CSYYQSC (SEQ ID NO:1) and an amino acid sequence represented by RGD (hereinafter simply referred to as an RGD sequence); and (2) a second region including (2-i) an amino acid sequence represented by PRPSLAKKQRFRHRNRKGYR-SQRGHSRGRNQN (SEQ ID NO:2), (2-ii) an amino acid sequence having an identity of not less than 50% to an amino acid sequence represented by SEQ ID NO:2 and having an adsorption ability to a cultivation container, or (2-iii) an amino acid sequence that is the amino acid sequence represented by SEQ ID NO:2, in which from 1 to 30 amino acid residues are added, substituted, or deleted, and that has an adsorption ability to a cultivation container.

The first region contains at least one selected from the group consisting of an amino acid sequence represented by SEQ ID NO:1 and an RGD sequence.

The amino acid sequence represented by SEQ ID NO:1 corresponds to from 25th to 31th seven amino acid residues in the amino acid sequence of vitronectin. The RGD sequence is a cell-adhesive motif corresponding to from 45th to 47th three amino acid residues in the amino acid sequence of vitronectin. Each of the amino acid sequences is a sequence located in a site relatively closer to the N-terminal in natural vitronectin, exhibits adhesiveness in an undifferentiated pluripotent stem cell, and is thus presumed to enable pluripotent stem cells maintained in an undifferentiated state to proliferate. Therefore, polypeptides that contain none of the amino acid sequences are poor in cell adhesiveness and are incapable of offering the advantages of the invention. However, the invention is not restricted by this theory.

Two cysteine residues in the amino acid sequence represented by SEQ ID NO:1 may be cross-linked with each other. As a result, a higher-order structure, which improves adhesiveness to pluripotent stem cells, tends to be formed in the amino acid sequence represented by SEQ ID NO:1.

As used herein, the expression "enable pluripotent stem cells to proliferate in undifferentiated state" means that pluripotent stem cells maintain differentiation potency in a culture period. Whether or not pluripotent stem cells are in an undifferentiated state can be determined by a known evaluation method. For example, the determination is performed by a method known to those skilled in the art, such as expression of a molecular marker (e.g., assay of expression by flow cytometry for SSEA-4, Oct-4, and/or the like, or immunostaining for Oct-4, NANOG, and/or the like), confirmation of pluripotent differentiation by an in vitro experiment, or confirmation of teratocarcinogenesis due to transplantation into immunodeficient mice and the like. Whether or not the proliferation is caused may be determined by visual observation using various microscopes by usual methods, a response test for ALP activity or the like, a technique utilizing flow cytometry or the like, or another technique. A culture period in which the differentiation potency of pluripotent stem cells in the invention is maintained varies according to culture conditions and the cell state of the pluripotent stem cells, and may be allowed to be a culture period of e.g., 1 month.

It is sufficient that the first region in the polypeptide for use in culture contains any one selected from the group consisting of the amino acid sequence represented by SEQ ID NO:1 and the RGD sequence. From the viewpoint of cell adhesiveness and cell proliferation properties, it is preferable that the first region in the polypeptide for use in culture contains both of the sequences.

The first region may contain an amino acid sequence which is different from the amino acid sequence represented by SEQ ID NO:1 and the RGD sequence. Examples of such different amino acid sequences include (1a) an amino acid sequence consisting of the 1st to 24th amino acid residues, (1b) an amino acid sequence consisting of the 48th to 55th amino acid residues, (1c) an amino acid sequence consisting of the 32th to 44th amino acid residues, in the amino acid sequence of human vitronectin, shown in SEQ ID NO:3, and combinations thereof, from the viewpoint of the cell adhesiveness and cell proliferation properties of the first region. Each of the amino acid sequences from (1a) to (1c) may have a sequence in which from 1 to 30 amino acid residues are substituted, deleted, or eliminated so that the cell adhesiveness and cell proliferation properties of the first region are not deteriorated, and may have an amino acid sequence having an identity of not less than 50% to each sequence of the amino acid sequences from (1a) to (1c).

The first region can contain, in addition to the amino acid sequence represented by SEQ ID NO:1 and the RGD sequence, at least one selected from the group consisting of the amino acid sequences of from (1a) to (1c), and preferably contains both of the amino acid sequence represented by SEQ ID NO:1 and the RGD sequence, and an amino acid sequence consisting of the 1st to 55th amino acid residues in the amino acid sequence represented by SEQ ID NO:3, or an amino acid sequence that is similar thereto or part thereof, from the viewpoint of cell adhesiveness and cell proliferation properties.

The number of amino acid residues in the first region, the number of the amino acid residues can be from 3 to 60 from the viewpoint of cell adhesiveness and proliferation properties, and preferably from 10 to 55.

The second region contains the amino acid sequence represented by SEQ ID NO:2 and consisting of 32 amino acid residues, and preferably consists of the amino acid sequence represented by SEQ ED NO:2 from the viewpoint of the easiness of purification of the polypeptide for use in culture. The amino acid sequence represented by SEQ ID NO:2 is contained in a part of hemopexin-like domain II located in a site closer to the C-terminal of natural vitronectin, and corresponds to a heparin binding domain including from 342nd to 373rd amino acid residues in the amino acid sequence represented by SEQ ID NO:3. Hereinafter, the amino acid sequence represented by SEQ ID NO:2 may be referred to as a heparin binding domain.

It is presumed that the polypeptide for use in culture has an adsorption ability to a cultivation container because of having the heparin binding domain. As a result, undifferentiated pluripotent stem cells can be cultured for a long term while maintaining an undifferentiated state. However, the invention is not restricted by this theory.

The polypeptide for use in culture tends to assure the hydrophilicity of the polypeptide for use in culture, to suppress the hydrophobic aggregation of the polypeptide, because of containing the heparin binding domain. As a result, the purification of the polypeptide for use in culture is facilitated, and production efficiency can be enhanced.

As used herein, the expression "having adsorption ability to cultivation container" means that the amino acid sequence can be physically adsorbed to a cell culture surface (hereinafter also simply referred to as a "culture surface") of a cultivation container of interest without chemical reaction. Whether or not to have an adsorption ability to a culture surface of a cultivation container can be evaluated by, for example, determining whether or not 10 pmol/cm$^2$ or more of the polypeptide remaining on a surface of a polystyrene cultivation container subjected to plasma treatment is present in a case in which a solution containing the polypeptide is added to the culture plate so that the polypeptide is 200 pmol/cm², left to stand at 37° C. for 2 hours, and then washed twice with a phosphate buffer.

The amount of the polypeptide remaining on the surface of the culture plate can be assayed by an ELISA (Enzyme-Linked Immunosorbent Assay) method in which the conjugation amount of antibody that recognizes the polypeptide is quantitated, or by hydrolyzing the adsorbed polypeptide and quantitating generated amino acids by HPLC or the like.

The heparin binding domain may be an amino acid sequence having an identity of not less than 50%, preferably not less than 80%, more preferably not less than 90%, still more preferably not less than 95% to the amino acid sequence represented by SEQ ID NO:2, enabling pluripotent stem cells to proliferate in an undifferentiated state, and having an adsorption ability to a cultivation container.

In addition, the heparin binding domain may comprise an amino acid sequence that is the amino acid sequence represented by SEQ ID NO:2 in which from 1 to 30, preferably from 1 to 15, and preferably from 1 to 6 amino acids are deleted, substituted, or added, and may be an amino acid sequence having an adsorption ability to a cultivation container.

It is sufficient for the polypeptide to have the first region and the second region. The relative positions of the regions are not particularly limited. In the polypeptide for use in culture, the first region is preferably located at an N-terminal side of the second region.

The polypeptide for use in culture consists of from 40 to 450 amino acid residues. In the case of less than 40 amino acid residues, cell adhesiveness, a cell proliferation property, or an adsorption ability to a cultivation container may be insufficient. In the case of more than 450 amino acid residues, cell adhesiveness or a cell proliferation property, and an adsorption ability to a cultivation container may be prevented from being suitably exerted, and association, crosslinking, or aggregation between proteins is facilitated. The polypeptide for use in culture preferably includes 80 or more, more preferably 90 or more, still more preferably 100 or more, and preferably 400 or less, more preferably 250 or less, still more preferably 170 or less, even more preferably 150 or less amino acid residues from the viewpoint of inhibiting the aggregation or the like. Any of the upper or lower limits may be combined. For example, the polypeptide preferably consists of from 40 to 400 amino acid residues, more preferably consists of from 80 to 250 amino acid residues, still more preferably consists of from 80 to 150 amino acid residues, and even more preferably consists of from 100 to 150 amino acid residues.

It is preferable that the polypeptide for use in culture has a GRAVY value of from −2.0 to −0.95 from the viewpoint of preventing hydrophobic aggregation. A GRAVY value (Kyte J., Doolittle R. F. (1982), J. Mol. Biol, 157: 105-132) represents a gross mean hydrophobicity of a polypeptide. A higher GRAVY value means higher hydrophobicity. A GRAVY value of −0.95 or less results in a tendency to be capable of easily suppressing occurrence of hydrophobic aggregation. In contrast, a GRAVY value of −2.0 or more facilitates adsorption to a surface of a cultivation container and proliferation of undifferentiated cells. The adsorptivity and cell proliferation properties tend to be improved with increasing the GRAVY value. The GRAVY value of the polypeptide is more preferably from −1.70 to −0.975, and still more preferably from −1.60 to −1.10, in view of compatibility between the suppression of aggregation and adsorptivity or cell proliferation properties. Since more aggregation tends to occur with decreasing the number of amino acid residues, the GRAVY value is preferably from −1.70 to −0.975, and still more preferably from −1.60 to −1.10, in view of compatibility between the suppression of aggregation and adsorptivity or cell proliferation properties, in a case in which the polypeptide comprises from 80 to 170 amino acid residues.

A GRAVY value can be adjusted, for example, by increasing or decreasing the rate of hydrophobic amino acids (e.g., Trp, Tyr, Phe, Leu, Ile, Val, or Met), or by increasing or decreasing the number of amino acid residues, in a sequence.

It is preferable that the polypeptide for use in culture further has an amino acid sequence which is different from the first region and the second region. It is preferable that the polypeptide for use in culture includes a polypeptide shown in SEQ ID NO:3, i.e., a partial sequence in the amino acid sequence of human vitronectin, from the viewpoint of suitably exerting cell adhesiveness and an adsorption ability to a cultivation container. As a result, the polypeptide for use in culture can acquire properties similar to those of human vitronectin, for example, excellent adhesiveness to pluripotent stem cells, and proliferation properties.

From the viewpoint of the cell adhesiveness and cell proliferation properties of the polypeptide for use in culture, an adsorption ability to a cultivation container, or the suppression of aggregation, the partial amino acid sequence in human vitronectin that can be contained in the polypeptide for use in culture preferably includes at least one selected from the group consisting of the following third and fourth regions:

(3) a third region consisting of an amino acid sequence selected from an amino acid sequence consisting of the 56th to 341st341st amino acid residues in the amino acid sequence represented by SEQ ID NO:3, or a partial amino acid sequence thereof; and (4) a fourth region consisting of an amino acid sequence selected from an amino acid sequence consisting of the 374th to 459th amino acid residues in the amino acid sequence represented by SEQ ID NO:3, or a partial amino acid sequence thereof.

For the third region, (3a) an amino acid sequence consisting of the 132th to 341st amino acid residues in the amino acid sequence represented by SEQ ID NO:3, or a partial amino acid sequence thereof, (3b) an amino acid sequence consisting of the 269th to 341st amino acid residues, or a partial amino acid sequence thereof, (3c) an amino acid sequence consisting of the 274th to 341st amino acid residues, or a partial amino acid sequence thereof can be selected, or (3d) an amino acid sequence consisting of the 294th to 341st amino acid residues, or a partial amino acid sequence thereof is acceptable, from the viewpoint of a tendency to suppress hydrophobic aggregation in a case in which the polypeptide is produced. Hydrophobic aggregation tends to be able to be reduced by reducing the number of amino acid residues in the amino acid sequences from (3a) to (3d). Especially, the selection of the amino acid sequence (3d) is preferred since hydrophobic aggregation tends to be able to be more reliably suppressed.

The fourth region can be an amino acid sequence consisting of the 374th to 459th amino acid residues, or a partial amino acid sequence thereof, an amino acid sequence consisting of the 374th to 409th amino acid residues, or a partial amino acid sequence thereof, or an amino acid sequence consisting of the 374th to 379th amino acid residues, or a partial amino acid sequence thereof, from the viewpoint of adsorptivity to a culture plate.

Especially, from the 374th to 379th amino acid residues are preferred in view of adsorptivity to a culture plate as well as easiness of suppressing hydrophobic aggregation in a case in which the polypeptide is produced, and hydrophobic aggregation tends to be reduced by reducing the number of selected amino acids.

Each of the partial amino acid sequences in the amino acid sequences included in the third and fourth regions means an amino acid sequence including three or more consecutive amino acid residues in amino acid residues in the specific range. The number of the amino acid residues in each of the partial amino acid sequences may be selected so as not to be more than the total number of the amino acid residues of the polypeptide for use in culture mentioned above.

The amino acid sequence and partial amino acid sequence thereof included in each of the third and fourth regions may be an amino acid sequence or partial amino acid sequence thereof having a identity of preferably not less than 80%, more preferably not less than 90%, more preferably not less than 95%, still more preferably not less than 95% to the respective amino acid sequence or partial sequence thereof. These amino acid sequences can be selected so that the cell adhesiveness and adsorptivity to a cultivation container of the polypeptide for use in culture are not deteriorated.

The amino acid sequence and partial amino acid sequence thereof, included in each of the third and fourth regions, may be an amino acid sequence that is the respective amino acid sequence or partial sequence thereof in which from 1 to 30, preferably from 1 to 15, more preferably from 1 to 5 amino acid residues are deleted, substituted, or added. The amino acid sequence in which the amino acid residues are subjected to deletion or the like can be selected so that the cell adhesiveness and adsorptivity to a cultivation container, of the polypeptide for use in culture, are not deteriorated.

The polypeptide for use in culture tends to have an advantage of enhancing adsorptivity to a culture plate because the polypeptide for use in culture contains the third region. The polypeptide for use in culture tends to have an advantage of further enhancing adsorptivity to a culture plate because of containing the fourth region. It is sufficient for the polypeptide for use in culture to contain either third or fourth region.

The GRAVY value of the polypeptide for use in culture is preferably adjusted, for example, by increasing or decreasing the number of amino acid residues in the amino acid sequences included in the third and fourth regions, or by substituting deleting, or adding amino acid residues, and it is more preferable to particularly adjust the length of the amino acid sequence included in the third region, from the viewpoint of the easiness of adjustment.

The polypeptide for use in culture does not necessarily contain from 56th to 131th amino acid residues, from 56th to 268th amino acid residues, from the 269th to 273th amino acid residues, and/or from the 50th to 293th amino acid residues, in the amino acid sequence represented by SEQ ID NO:3. An amino acid sequence consisting of the amino acid residues is presumed not to contribute to the feature of the polypeptide for use in culture for the culture of pluripotent cells, and a suitable sequence is selected from the viewpoint of adsorption to a culture plate.

In a case in which the third region contains an amino acid residue corresponding to a cysteine residue in the sequence represented by SEQ ID NO:3, an amino acid residue different from a cysteine residue may be located at the position of the cysteine residue. As a result, intramolecular or intermolecular crosslinking due to the cysteine residue can be preferably prevented from being formed. Examples of the different amino acid residue for substituting the cysteine residue are not particularly limited but include a serine residue, an alanine residue, and a glycine residue. Especially, a serine residue or an alanine residue is preferred in view of having a structure similar to that of cysteine.

The polypeptide for use in culture may also comprise arbitrary additional amino acid residues other than the above as long as cell adhesiveness and adsorptivity to a cultivation container are not deteriorated thereby. Examples of sequences consisting of such other arbitrary amino acid residues include additional sequences added for easily producing the polypeptide for use in culture by a recombinant technology. Examples of such additional sequences include N-terminal methionine residues, N-terminal GPLG (SEQ ID NO: 40) sequences, tag sequences (for example, GST (glutathione S-transferase), FLAG tag, His tag, and the like), and linker sequences that can be added between regions (for example, GGGS (SEQ ID NO: 41), GGGGS (SEQ ID NO: 42), GGGGGS (SEQ ID NO: 43), and the like).

The polypeptide for use in culture can be produced by an amino acid synthesis technology or gene-recombination technology known to those skilled in the art.

In a case in which the polypeptide for use in culture of the invention is obtained by the gene-recombination technology, specifically, first, genes encoding an amino acid sequence of interest are acquired and incorporated into an expression vector to produce a recombinant expression vector, which is introduced into an appropriate host to produce a transformant. The obtained transformant is cultured in an appropriate culture medium, to thereby produce a polypeptide of interest, and the polypeptide of interest is therefore collected from the culture by a usual method, whereby the polypeptide according to the invention can be obtained.

It is preferable that the polypeptide for use in culture is a polypeptide (A) consisting of from 80 to 450 amino acid residues, in which the polypeptide (A) includes: (1) the first region consisting of an amino acid sequence consisting of the 25th to 47th amino acid residues in the amino acid sequence represented by SEQ ID NO:3; (2) the second region consisting of an amino acid sequence consisting of the 342nd to 373rd amino acid residues in the amino acid sequence represented by SEQ ID NO:3; and at least one selected from the group consisting of the following third and fourth regions: (3) the third region consisting of an amino acid sequence consisting of the 269th to 341st amino acid residues in the amino acid sequence represented by SEQ ID NO:3, or a partial amino acid sequence thereof; and (4) the fourth region consisting of an amino acid sequence consisting of the 374th to 459th amino acid residues in the amino acid sequence represented by SEQ ID NO:3, or a partial amino acid sequence thereof, from the viewpoint of cell proliferation properties, the proliferation potency of undifferentiated pluripotent stem cells in an undifferentiated state, and the like.

It is preferable that the polypeptide for use in culture is a polypeptide (B) consisting of the 100 to 450 amino acid residues, in which the polypeptide (B) comprises: (1) the first region consisting of an amino acid sequence consisting of the 1st to 55th amino acid residues in the amino acid sequence represented by SEQ ID NO:3 (containing the amino acid sequence represented by SEQ ID NO:1 and the RGD sequence); (2) the second region (heparin binding domain) consisting of an amino acid sequence consisting of the 342nd to 373rd amino acid residues in the amino acid sequence represented by SEQ ID NO:3; and at least one selected from the group consisting of the following third and fourth regions: (3) the third region consisting of an amino acid sequence consisting of the 269th to 341st amino acid residues in the amino acid sequence represented by SEQ ID NO:3, or a partial amino acid sequence thereof; and (4) the fourth region consisting of an amino acid sequence consisting of the 374th to 459th amino acid residues in the amino acid sequence represented by SEQ NO:3, or a partial amino acid sequence thereof, from the viewpoint of cell proliferation properties, the proliferation potency of undifferentiated pluripotent stem cells in an undifferentiated state, and the like.

It is preferable that the polypeptide (A) or (B) is a polypeptide further having a GRAVY value of from −2.0 to −0.95.

It is preferable that the polypeptide (A) consists of from 80 to 250 amino acid residues.

It is preferable that the polypeptide (A) is a polypeptide further having a GRAVY value of from −2.0 to −0.95 and consisting of from 80 to 250 amino acid residues.

It is preferable that the polypeptide (A) is a polypeptide further having a GRAVY value of from −1.70 to −0.975 and consisting of from 80 to 250 amino acid residues.

It is preferable that the polypeptide (A) or (B) consists of from 100 to 250 amino acid residues.

It is preferable that the polypeptide (A) or (B) is a polypeptide further having a GRAVY value of from −2.0 to −0.95 and consisting of from 100 to 250 amino acid residues.

It is preferable that the polypeptide (A) or (B) is a polypeptide further having a GRAVY value of from −1.70 to −0.975 and consisting of from 100 to 250 amino acid residues.

It is preferable that the polypeptide (A) or (B) is a polypeptide further having a GRAVY value of from −1.70 to −0.975 and consisting of from 100 to 170 amino acid residues.

Examples of the polypeptide for use in culture are given below. However, the invention is not limited thereto.

TABLE 1

| Amino Acid Sequence | SEQ ID No. |
|---|---|
| DQESCKGRCTEGFNVDKKCQCDELGSYYQSCCTDYTAECKPQ VTRGDVFTMPEDEPSQEECEGSSLSAVFEHFAMMQRDSWEDI FELLFWGRTSAGTRQPQFISRDWHGVPGQVDAAMAGRIYISG MAPRPSLAKKQRFRHRNRKGYRSQRGHSRGRNQNSRRPSRAT WLSLFSSEESNLGANNYDDYRMDWLVPATCEPIQSVFFFSGD KYYRVNLRTRRVDTVDPPYPRSIAQYWLGCPAPGHL | 4 |
| DQESCKGRCTEGFNVDKKCQCDELCSYYQSCCTDYTAECKPQV TRGDVFTMPEDEPRPSLAKKQRFRHRNRKGYRSQRGHSRGRNQ N | 5 |
| DQESCKGRCTEGFNVDKKCQCDELCSYYQSCCTDYTAECKPQ VTRGDVFTMPEDEGVPGQVDAAMAGRIYISGMAPRPSLAKKQ RFRHRNRKGYRSQRGHSRGRNQN | 6 |
| DQESCKGRCTEGFNVDKKCQCDELCSYYQSCCTDYTAECKPQ VTRGDVFTMPEDEQPQFISRDWHGVPGQVDAAMAGRIYISGM APRPSLAKKQRFRHRNRKGYRSQRGHSRGRNQN | 7 |
| DQESCKGRCTEGFNVDKKCQCDELCSYYQSCCTDYTAECKPQ VTRGDVFTMPEDEFWGRTSAGTRQPQFISRDWHGVPGQVDAA MAGRIYISGMAPRPSLAKKQRFRHRNRKGYRSQRGHSRGRNQN | 8 |
| DQESCKGRCTEGFNVDKKCQCDELCSYYQSCCTDYTAECKPQ VTRGDVFTMPEDESQEESEGSSLSAVFEHFAMMQRDSWEDIF ELLFWGRTSAGTRQPQFISRDWHGVPGQVDAAMAGRIYISGM APRPSLAKKQRFRHRNRKGYRSQRGHSRGRNQNSRRPSRATW LSLFSSEESNLGANNYDDYRMDWLVPATSEPIQSVFFFSGDK YYRVNLRTRRVDTVDPPYPRSIAQYWLGSPAPGHL | 9 |

TABLE 1-continued

| Amino Acid Sequence | SEQ ID No. |
|---|---|
| DQESCKGRCTEGFNVDKKCQCDELCSYYQSCCTDYTAECKPQ VTRGDVFTMPEDESQEESEGSSLSAVFEHFAMMQRDSWEDIF ELLFWGRTSAGTRQPQFISRDWHGVPGQVDAAMAGRIYISGM APRPSLAKKQRKRHRNRKGYRSQRGHSRGRNQN | 10 |
| DQESCKGRCTEGFNVDKKCQCDELGSYYQSCCTDYTAECKPQ VTRGDVFTMPEDESQEESEGSSLSAVFEHFAMMQRDSWEDIF ELLFWGRTSAGTRQPQFISRDWHGVPGQVDAAMAGRIYISGM APRPSLAKKQRFRHRNRKGYRSQRGHSRGRNQNSRRPSR | 11 |
| DQESGKGRCTEGFNVDKKCQCDELGSYYQSCCTDYTAECKPQ VTRGDVFTMPEDESQEESEGSSLSAVFEHFAMMQRDSWEDIF ELLFWGRTSAGTRQPQFISRDWHGVPGQVDAAMAGRIYISGM APRPSLAKKQRFRHRNRKGYRSQRGHSRGRNQNSRRPSRATW LSLFSSE | 12 |
| DQESCKGRCTEGFNVDKKCQCDELCSYYQSCCTDYTAECKPQ VTRGDVFTMPEDESQEESEGSSLSAVFEHFAMMQRDSWEDIF ELLFWGRTSAGTRQPQFISRDWHGVPGQVDAAMAGRIYISGM APRPSLAKKQRFRHRNRKGYRSQRGHSRGRNQNSRRPSRATW LSLFSSEESNLGANNYD | 13 |
| DQESCKGRCTEGFNVDKKCQCDELCSYYQSCCTDYTAECKPQ VTRGDVFTMPEDESQEESEGSEDIFELLFWGRTSAGTRQPQF ISRDWHGVPGQVDAAMAGRIYISGMAPRPSLAKKQRFRHRNR KGYRSQRGHSRGRNQN | 38 |

<Method of Culturing Pluripotent Stem Cells>

The method of culturing a pluripotent stem cell of the invention includes: applying the polypeptide for use in culture to a cell culture surface of a support, to obtain a culture surface coated with the polypeptide for use in culture (hereinafter referred to as a culture surface preparation step); and seeding a pluripotent stem cell on the culture surface coated with the polypeptide for use in culture and culturing the pluripotent stem cell (hereinafter referred to as a culture step).

In the culture method of the invention, the polypeptide for use in culture, which has the first domain which enables pluripotent stem cells to be retained in an undifferentiated state and the second domain which enables favorable adsorption to a cultivation container, is adsorbed to the culture surface, and pluripotent stem cells are seeded and cultured thereon. Therefore, the pluripotent stem cells can be cultured with maintaining an undifferentiated state while suppressing removal of the pluripotent stem cells due to separation thereof from the cell culture surface.

The pluripotent stem cells that can be proliferated in a retained undifferentiated state by culturing the pluripotent stem cells on the polypeptide for use in culture according to the invention are the pluripotent stem cells of primate animals, and specifically encompasses embryonic stem cells (ES cells), induced pluripotent stem cells (iPS cells), somatic stem cells, fertilized egg inner cell mass cells, early embryonic cells, and the like. One kind of the cells may be used, or two or more kinds of the cells may be used in admixture, if necessary. The iPS cells encompass cells described in Nature, 2007, Jul. 19; Vol. 448, pp. 313-317; Cell, 2006, Aug. 25; Vol. 126(4), pp. 663-676, or cells similar thereto.

Especially, examples of pluripotent stem cells that are preferably applied in the invention include iPS cells.

Examples of primate animals include human, monkey, and gorilla, and human congeneric to the polypeptide for use in culture is particularly preferred. The component or substance applied to the invention can be preferably applied as a component or substance derived from a homologous animal to the invention in a case in which the component or substance applied to the invention is a component or substance derived from a primate animal.

A culture liquid used for culture can be appropriately selected depending on the kind of a cell to be cultured. The culture liquid that can be used may be any known culture liquid, and examples thereof include DMEM, MEM, F12, DME, RPMI1640, MCDB104, 199, MCDB153, L15, SkBM, and Basal medium. To these culture liquids, various components that can be generally added, such as glucose, FBS (fetal bovine serum) or human serum, and antibiotics (such as penicillin and streptomycin) may be added. A concentration of serum in a case of adding the serum can be appropriately varied, according to a culture state in the case, and can be typically set to 10% (v/v).

It is preferable to culture the pluripotent stem cells in the absence of a component derived from a heterologous animal in the culture method. Thereby, the possibility of a contamination of a foreign substance derived from a heterologous animal can be eliminated with high precision. Examples of the culture in the absence of a component derived from a heterologous cell include a culture in which a culture liquid that does not contain any component derived from a heterologous animal is used, and a culture in which feeder cells and the like derived from a heterologous animal are not used.

It is preferable to culture the pluripotent stem cells in the absence of a component derived from a heterologous animal and a serum component in the culture method. Thereby, a contamination of a component derived from a heterologous animal can be still more eliminated.

As the culture liquid that does not contain any component derived from a heterologous animal, a mixed culture medium including a hyposmotic culture medium containing at least one of medium components such as non-essential amino acids, glutamic acid, β-mercaptoethanol, FGF-2, TGF-β, insulin, and transferrin can be used. Specifically, a culture medium such as TeSR2 (StemCell Technologies, can be used. However, the culture liquid is not limited thereto.

A culture in an incubator under usual culture conditions, for example, at a temperature of 37° C. and a $CO_2$ concentration of 5% (v/v) is applied to the cell culture.

Usual culture media used for maintaining pluripotent stem cells can be used in methods of culturing and subculturing the pluripotent stem cells. Specific examples thereof include mTeSR and TeSR2 (StemCell Technologies, Inc.). The pluripotent stem cells are seeded in a culture medium by a usual method. The culture media used in a series of subcultures are not necessarily the same, and may be different culture media as long as the pluripotent stem cells can be maintained in an undifferentiated state.

The culture surface preparation step includes applying a coating solution containing a predetermined amount of the polypeptide for use in culture to a culture surface of a support. As a result, the culture surface can be coated with the polypeptide for use in culture. A content of the polypeptide for use in culture in the coating solution varies according to the kind or size of the culture surface to be coated, and is preferably from 1 pmol/cm² to 1000 pmol/cm², and more preferably from 100 pmol/cm² to 300 pmol/cm², from the viewpoint of an adsorption ability to the culture surface. An aqueous medium used for preparing the coating solution is not particularly limited, and examples thereof include phosphate buffers, Tris buffers, and ultrapure water.

It is sufficient that the coating solution is applied, and the coating is thereafter retained for predetermined time, for example, around from 30 minutes to 24 hours. Thereby, the culture surface can be coated with the polypeptide for use in culture without requiring a special treatment.

The culture step includes seeding the pluripotent stem cells on the culture surface coated with the polypeptide for use in culture, and culturing the pluripotent stem cells.

The seeding density and culture of the pluripotent stem cells are not particularly limited, and generally used conditions may be applied. The culture may be carried out under the culture and subculture conditions mentioned above, for example, at a seeding density of from around $1 \times 10^3$/cm² to $1 \times 10^5$/cm². A cell mass of from 10 μm to 100 μm may also be cultured under the culture and subculture conditions mentioned above at a seeding density of from around 1/cm² to 5/cm².

Thereby, the pluripotent stem cells can be favorably proliferated on the polypeptide for use in culture, with favorable handleability and in a maintained undifferentiated state.

<Cultivation Container>

In the invention, the cultivation container refers to a support having a surface to be used for cell culture. As such a support, a support well known as a support for cell culture in the art can be used as it is. Examples of the support may include plastics (for example, polystyrene, acrylonitrile-butadiene-styrene resins, polycarbonate resins, and polyester resins), glass, microporous filters (for example, cellulose, nylon, glass fibers, polyesters, and polycarbonates), materials for bioreactors (which may include hollow fiber tubes or microcarrier beads) used in cell culture in a batch-type or continuous-type process, or in genetic engineering (for example, bioreactors and the like), polyethylene terephthalate, Teflon registered trademark), ceramics, and related polymer materials.

The support may also be a support of which a culture surface is coated with a plasma polymerized thin film.

A form of the cultivation container is not particularly limited, and may be any form that can be applied to the culture of the pluripotent stem cells. Examples of containers with such forms include multi-well plates (for example, 6-well, 12-well, 24-well, and 96-well), culture plates (for example, petri dishes and the like), tubes, culture flasks, roller bottles, and shake culture flasks.

The cultivation container according to the invention has a support having a cell culture surface, and the polypeptide for use in culture, placed on the cell culture surface of the support.

Since the cultivation container has the culture surface provided with the polypeptide for use in culture according to the invention, the polypeptide for use in culture is favorably adsorbed to the culture surface, and pluripotent stem cells can be proliferated with favorable handleability and in a maintained undifferentiated state in a case in which the pluripotent stem cells are seeded on the polypeptide for use in culture.

As used herein, the culture surface in the cultivation container means a surface to which cells can adhere in a case in which the seeded cells are grown.

The cultivation container according to the invention can be produced by a production method including: preparing a material provided with a support having a cell culture surface (hereinafter "preparation step"); and applying the polypeptide for use in culture to the cell culture surface, to perform adsorption treatment (hereinafter "adsorption treatment step"). As a result, the cultivation container according to the invention can be easily obtained.

In the preparation step, the cultivation container provided with the support having the culture surface is prepared. In a case in which the support has a plasma polymerized thin film on the culture surface, a step of forming the plasma polymerized thin film on the support may be included therein. To the method of forming the plasma polymerized thin film, a usual method may be applied without being changed.

The adsorption treatment step comprises applying the polypeptide for use in culture according to the invention to the culture surface, and retaining the polypeptide for use in culture. In the adsorption treatment step, an adsorption liquid containing a predetermined amount of the polypeptide for use in culture may be prepared, applied to the culture surface, and retained for predetermined time, to thereby adsorb the polypeptide for use in culture to the culture surface.

The explanation of the step of preparing the culture surface coated with the polypeptide for use in culture in the culture method can be applied to the adsorption treatment step as it is.

EXAMPLES

The invention will be described in detail below by examples. However, the invention is not limited to these examples. Unless otherwise specified, "%" is based on mass.

Example 1

<Preparation of Polypeptide>

A gene sequence encoding each polypeptide of from RCP-1 to RCP-17 having amino acid sequences listed in Table 2 and Table 3 was amplified by a usual method utilizing PCR. RCP-11 corresponds to the sequence of natural human vitronectin. A position corresponding to the amino acid sequence of each polypeptide in the amino acid sequence (SEQ ID NO:3) of natural human vitronectin is listed in each "NOTE" box in Table 2 and Table 3. It is remarked that the amino acid sequences of the polypeptides may include an amino acid sequence which is the amino acid sequence of a corresponding range in natural human vitronectin as described in each table and to which addition, deletion, or substitution is performed. Each of from RCP-1 to RCP-10, and RCP-17 has the same amino acid sequence as each of the amino acid sequences shown in SEQ ID NOs: 4 to 13 and SEQ ID NO:38 mentioned above except that methionine is present at position 1.

For from RCP-1 to RCP-10, and RCP-17, genes of interest were inserted into pET-28b (+), previously subjected to cleavage treatment with NcoI (Takara Bio Inc.), using an InFusion Advantage PCR Cloning Kit (Clontech), to construct each vector for expression. For from RCP-11 to RCP-16, genes of interest were inserted into pGEX-6P-1 (GE Healthcare) previously subjected to cleavage treatment with BamHI (Takara Bio Inc.) by the same technique as described above, to construct each vector for expression. The sequence of each vector for expression was confirmed by sequence analysis.

TABLE 2

| | | Amino Acid Sequence | SEQ ID NO: | NOTE |
|---|---|---|---|---|
| The Invention | RCP-1 | MDQESCKGRCTEGFNVDKKCQCDELCSYYQSCCTDYTAECKPQVTRGDVFT MPEDEPSQEECEGSSLSAVFEHFAMMQRDSWEDIFELLFWGRTSAGTRQPQ FISRDWHGVPGQVDAAMAGRIYSGMAPRPSLAKKQRFRHRNRKGYRSQRGH SRGRNQNSRRPSRATWLSLFSSEESNLGANNYDDYRMDWLVPATCEPIQSV FFFSGDKYYRVNLRTRRVDTVDPPYPRSIAQYWLGCPAPGHL | 14 | 1-55 269-459 |
| | RCP-2 | MDQESCKGRCTEGFNVDKKCQCDELCSYYQSCCTDYTAECKPQVTRGDVFT MPEDEPRPSLAKKQRFRHRNRKGYRSQRGHSRGRNQN | 15 | 1-55 342-373 |
| | RCP-3 | MDQESCKGRCTEGFNVDKKCQCDELCSYYQSCCTDYTAECKPQVTRGDVFT MPEDEGVPGQVDAAMAGRIYISGMAPRPSLAKKQRFRHRNRKGYRSQRGHS RGRNQN | 16 | 1-55 322-341 342-373 |
| | RCP-4 | MDQESCKGRCTEGFNVDKKCQCDELCSYYQSCCTDYTAECKPQVTRGDVFT MPEDEQPQFISRDWHGVPGQVDAAMAGRIYISGMAPRPSLAKKQRFRHRNR KGYRSQRGHSRGRNQN | 17 | 1-55 312-341 342-373 |
| | RCP-5 | MDQESCKGRCTEGFNVDKKCQCDELCSYYQSCCTDYTAECKPQVTRGDVFT MPEDEFWGRTSAGTRQPQFISRDWHGVPGQVDAAMAGRIYISGMAPRPSLA KKQRFRHRNRKGYRSQRGHSRGRNQN | 18 | 1-55 302-341 342-373 |
| | RCP-6 | MDQESCKGRCTEGFNVDKKCQCDLECSYYQSCCTDYTAECKPQVTRGDVFT MPEDESQEESEGSSLSAVFEHFAMMQRDSWEDIFELLFWGRTSAGTRQPQF ISRDWHGVPGQVDAAMAGRIYISGMAPRPSLAKKQRFRHRNRKGYRSQRGH SRGRNQNSRRPSRATWLSLFSSEESNLGANNYDDYRMDWLVPATSEPIQSV FFFSGDKYYRVNLRTRRVDTVDPPYPRSIAQYWLGSPAPGHL | 19 | 1-55 269-459 C274S |
| | RCP-7 | MDQESCKGRCTEGFNVDKKCQCDELCSYYQSCCTDYTAECKPQVTRGDVFT MPEDESQEESEGSSLSAVFEHFAMMQRDSWEDIFELLFWGRTSAGTRQPQF ISRDWHGVPGQVDAAMAGRIYISGMAPRPSLAKKQRFRHRNRKGYRSQRGH SRGRNQN | 20 | 1-55 269-373 C274S |
| | RCP-8 | MDQESCKGRCTEGFNVDKKCQCDELSCYYQSCCTDYTAECKPQVTRGDVFT MPEDESQEESEGSSLSAVFEHFAMMQRDSWEDIFELLFWGRTSAGTRQPQF ISRDWHGVPGQVDAAMAGRIYISGMAPRPSLAKKQRFRHRNRKGYRSQRGH SRGRNQNSRRPSR | 21 | 1-55 269-373 374-379 C274S |
| | RCP-9 | MDQESCKGRCTEGFNVDKKCQCDELCSYYQSCCTDYTAECKPQVTRGDVFT MPEDESQEESEGSSLSAVFEHFAMMQRDSWEDIFELLFWGRTSAGTRQPQF | 22 | 1-55 269-373 |

TABLE 2-continued

| | Amino Acid Sequence | SEQ ID NO: | NOTE |
|---|---|---|---|
| | ISRDWHGVPGQVDAAMAGRIYISGMAPRPSLAKKQRFRHRNRKGYRSQRGH SRGRNQNSRRPSRATWLSLFSSE | | 374-389 C274S |
| RCP-10 | MDQESCKGRCTEGFNVDKKCQCDELCSYYQSCCTDYTAECKPQVTRGDVFT MPEDESQEESEGSSLSAVFEHFAMMQRDSWEDIFELLFWGRTSAGTRQPQF ISRDWIGVPGQVDAAMAGRIYISGMAPRPSLAKKQRFRHRNRKGYRSQRGH SRGRNQNSRRPSRATWLSLFSSEESNLGANNYD | 23 | 1-55 269-373 374-399 C274S |
| RCP-11 | MDQESCKGRCTEGFNVDKKCQCDELCSYYQSCCTDYTAECKPQVTRGDVFT MPEDESQEESEGSEDIFELLFWGRTSAGTRQPQFISRDWHGVPGQVDAAMA GRIYISGMAPSPSLAKKQRFRHRNRKGYRSQRGHSRGRNQN | 39 | 1-55 269-277 295-341 342-373 C274S |

TABLE 3

| | Amino Acid Sequence | SEQ ID NO: | NOTE |
|---|---|---|---|
| Comparative Example RCP-11 | GPLGDQESCKGRCTEGFNVDKKCQCDELCSYYQSCCTDYTAECKPQVTRGD VFTMPEDEYTVYDDGEEKNNATVHEQVGGPSLTSDLQAQSKGNPEQTPVLK PEEEAPAPEVGASKPEGIDSRPETLHPGRPQPPAEEELCSGKPFDAFTDLK NGSLFAFRGQYCYELDEKAVRPGYPKLIRDVWGIEGPIDAAFTRINCQGKT YLFKGSQYWRFEDGVLDPDYPRNISDGFDGIPDNVDAALALPAHSYSGRER VYFFKGKQYWEYQFQHQPSQEECEGSSLSAVFEHFAMMQRDSWEDIFEELF WGRTSAGTRQPQFISRDWHGVPGQVDAAMAGRIYISGMAPRPSLAKKQRFR HRNRKGYRSQRGHSRGRNQNSRRPSRATWLSLFSSEESNLGANNYDDYRMD WLVPATCEPQISVFFFSGDKYYRVNLRTRRVDTVDPPYPRSIAQYWLGCPA PGHL | 24 | 1-459 |
| RCP-12 | GPLGDQESCKGRCTEGFNVDKKCQCDELCSYYQSCCTDYTAECKPQVTRGD VFTMPEDEYTVYDDGEEKNNATVHEQVGGPSLTSDLQAQSKGNPEQTPVLK PEEEAPAPEVGASKPEGIDSRPETLHPGRPQPPAEEELCSGKPFDAFTDLK NGSLFAFRGQYCYELDEKAVRPGYPKLIRDVWGIEGPIDAAFTRINCQGKT YLFKGSQYWRFEDGVLDPDYPRNISDGFDGIPDNVDAALALPAHSYSGRER VYFFKGKQYWEYQFQHQ | 25 | 1-55 56-268 |
| PCP-13 | GPLGDQESCKGRCTEGFNVDKKCQCDELCSYYQSCCTDYTAECKPQVTRGD VFTMPEDEYTVYDDGEEKNNATVHEQVGGPSLTSDLQAQSKGNPEQTPVLK PEEEAPAFEVGASKPEGIDSRPETLHPGRPQP | 26 | 1-55 56-129 |
| RCP-14 | GPLGDQESCKGRCTEGFNVDKKCQCDELCSYYQSCCTDYTAECKPQVTRGD VFTMPEDE | 27 | 1-55 |
| RCP-15 | GPLGYTVYDDGEEKNNATVHEQVGGPSLTSDLQAQSKGNPEQTPVLKPEEE APAPEVGASKPEGIDSRPETLHPGRPQPPAEEELCSGKPFDAFTDLKNGSL FAFRGQYCYELDEKAVRPGYPKLIRDVWGIEGPIDAAFTRINCQGKTYLFK GSQYWRFEDGVLDPDYPRNISDGFDGIPDNVDAALALPAHSYSGRERVYFF KGKQYWEYQFQHQPSQEECEGSSLSAVFEHFAMMQRDSWEDIFELLFWGRT SAGTRQPQFISRDWHGVPGQVDAAMAGRIYISGMAPRPSLAKKQRPRHRNR KGYRSQRGHSRGRNQNSRRPSRATWLSLFSSEESNLGANNYDDYRMDWLVP ATCEPIQSVFFFSGDKYYRVNLRTRRVDTVDPPYPRSIAQYWLGCPAPGHL | 28 | 56-459 |
| RCP-16 | GPLGPSQEECEGSSLSAVFEHFAMMQRDSWEDIFELLFWGRTSAGTRQPQF ISRDWHGVPGQVDAAMAGRIYISGMAPRPSLAKKQRFRHRNRKGYRSQRGH SRGRNQNSRRPSRATWLSLFSSEESNLGANNYDDYRMDWLVPATCEPIQSV FFFSGDKYYRVNLRTRRVDTVDPPYPRSIAQYWLGCPAPGHL | 29 | 269-459 |

Each of the produced expression vectors of from RCP-1 to RCP-10, and RCP-17 was transformed into BL21 (DE3) pLysS (Novagen) by a usual method, applied to a kanamycin-containing LB plate, and incubated at 37° C. for 16 hours. The introduction of each vector was confirmed by a colony direct PCR method, followed by adding 1 mM of IPTG (Wako Pure Chemical Industries, Ltd.) and by culturing the resultant with shaking at 37° C. for 5 hours, to induce the expression of a polypeptide.

A microbial body was collected by centrifugal treatment, and the microbial body was resuspended in a washing buffer (20 mM Tris, 150 mM NaCl, pH 7.6), The microbial body was crushed by sonication and thereafter centrifuged at 4° C. and 15000 rpm for 30 min, and an insoluble fraction was collected. The insoluble fraction was washed with a washing buffer containing 0.5 mass % of Triton X100, thereafter resuspended in a low-concentration urea buffer (Low Urea Buffer: 20 mM Tris, 150 mM NaCl, 2 M urea, pH 7.6), and subjected to sonication treatment. An insoluble fraction was collected by centrifugal treatment, followed by adding a high concentration urea buffer (High Urea Buffer: 20 mM Tris, 150 mM NaCl, 8 M urea, pH 7.6) thereto and by solubilizing the insoluble fraction by sonication treatment.

The solution containing a peptide of interest, obtained by the above-described method, was purified using an AKTA EXPLORER 100 (GE Healthcare) and a HITRAP HEPA- RIN HP 5 ml (GE Healthcare). Stepwise elution was performed with the high concentration urea buffer as a binding buffer and with a high-salt-concentration adjustment buffer (20 mM Tris, 1 M NaCl, 8 M urea, pH 7.6) as an elution buffer, to purify a polypeptide of interest.

Each of the expression vectors of from RCP-11 to RCP-16 produced as described above was transformed into BL21 (Novagen) by a usual method, applied to an ampicillin-containing LB plate, and incubated at 37° C. for 16 hours. The introduction of each vector was confirmed by a colony direct PCR method, followed by adding 100 μM of IPTG (isopropyl-β-D-thiogalactopyranoside) and by culturing the resultant with shaking at 20° C. for 24 hours, to induce the expression of a polypeptide.

A microbial body was collected and resuspended in B-PER (registered trademark) BACTERIAL PROTEIN EXTRACTION REAGENT in Phosphate Buffer (Thermo Scientific Inc.), followed by crushing the microbial body by sonication. The microbial body was centrifuged at 4° C. and 15000 rpm for 30 min, to remove an insoluble fraction. A supernatant was purified using an AKTA EXPLORER 100 and a GSTRAPHP 5 ml×2 (GE Healthcare). An elution fraction was desalted using a HIPREP 26/10 DESALTING (GE Healthcare), a protease for cleaving a GST fusion protein (PreScission Protease) was further added in 1/2000 of the amount of solution, and the resultant was incubated at 4° C. for 24 hours, to cleave a GST tag. Purification was performed in the GSTRAPHP 5 ml×2 again, and the cleaved GST tag was adsorbed to a column, and was removed. A fraction which passed through the column was dialyzed using a SLIDE-A-LIZER (3.5K MWCO.: Thermo Fisher Scientific Inc., the same applies hereafter), and buffer replacement was performed with PBS.

The polypeptide of RCP-1 obtained as described above was electrophoresed in a ready-made gel (12.5%, Bio-Rad), and was stained with GELCODE™ Blue Stain Reagent (Thermo Scientific Inc.). As a result, a single band was able to be recognized in a spot corresponding to a molecular weight of 28.3 kDa, which was expected from the amino acid sequence. Similar results were Obtained in the other polypeptides.

For from RCP-1 to RCP-10, and RCP-17, each polypeptide solution after the purification was dialyzed using a SLIDE-A-LIZER (3.5K MWCO). A dialysis external liquid was based on a dialysis buffer (PBS, 1.5 M NaCl, 0.5 M L-arginine, 1 mM EDTA, pH 7.4), and urea was removed by stepwise dialysis. The concentration of an end dialysis product was calculated at an absorbance of 280 nm using a NANODROP (Thremo Fisher Scientific Inc.). The presence or absence of aggregation after the dialysis is listed in Table 4.

A GRAVY value was calculated as a value obtained by dividing the total sum of hydrophobicity indices of which each is determined according to each amino acid by the number of amino acids (see Kyte J., Doolittle R. F. (1982), J. Mol. Biol, 157: 105-132). The GRAVY value is an index for the hydrophilicity and hydrophobicity of each polypeptide, calculated from the hydrophobicity of amino acids contained in each polypeptide, and the higher value exhibits a more hydrophobic property while the lower value exhibits a more hydrophilic property. The results are listed in Table 4.

In addition, the presence or absence of aggregation was evaluated by G, A, and B below. The results are also listed in Table 4.

G: Formation of an aggregate is not observed.

A: Formation of particles having a particle diameter of around 100 nm is observed.

B: Formation of visible aggregation with a particle diameter of 1 mm or more is observed.

TABLE 4

|  | GRAVY | The Number of Amino Acids | Aggregation |
| --- | --- | --- | --- |
| RCP-1 | −0.835 | 247 | A |
| RCP-2 | −1.516 | 88 | G |
| RCP-3 | −1.124 | 108 | G |
| RCP-4 | −1.150 | 118 | G |
| RCP-5 | −1.124 | 128 | G |
| RCP-6 | −0.875 | 246 | A |
| RCP-7 | −0.979 | 160 | A |
| RCP-8 | −1.045 | 166 | A |
| RCP-9 | −0.958 | 176 | B |
| RCP-10 | −0.971 | 186 | B |
| RCP-17 | −1.072 | 143 | A |

As listed in Table 4, it is found that each of from RCP-2 to RCP-5, from RCP-7 to RCP-8, and RCP-17 causes suppression of aggregation by having a GRAVY value of from −1.70 to −0.975, although it is a polypeptide consisting of from 80 to 170 amino acid residues, which should facilitate aggregation.

Example 2

<Evaluation of Adsorptivity to Culture Plate>

Each polypeptide obtained by the above-described method was diluted with a predetermined buffer so as to be added to wells at a predetermined final concentration of from 0 to 200 pmol/cm$^2$, and the resultant was aliquoted in 64 μL to a 96-well plate made of polystyrene and treated with plasma (Tissue Culture-Treated, Falcon). Each polypeptide was adsorbed to the plate by incubation at 37° C. for 2 hours, and was thereafter washed with PBS twice, to obtain a surface coated with each of the polypeptides of from RCP-1 to RCP-16.

To surfaces coated with RCP-1, and from RCP-11 to RCP-16 among the polypeptide-coated surfaces obtained as described above, 64 μL of each of boric acid buffer and 1 N NaOH was applied, and incubated at 80° C. and a humidity of 100% for 24 hours. After air-cooling, 75 μL of boric acid buffer was added to each well, and 50 μL of reaction liquid in which an OPA (o-phthalaldehyde: Wako Pure Chemical Industries, Ltd.)/methanol solution (160 mg/ml) and an NAC (N-acetyl-L-cysteine: Wako Pure Chemical industries, Ltd.)/boric acid buffer solution (2 mg/ml) were mixed at 1:100 (mass ratio) was further added. After incubation at 40° C. for 30 minutes, the fluorescence intensity thereof was measured (excitation of 355 nm/fluorescence of 486 nm) using an ENVISION MULTI-LABEL COUNTER (PerkinElmer Inc.). A calibration curve was separately made from each polypeptide solution, to calculate an amount of adsorption. The results are listed in FIG. 1. In FIG. 1, a black rhombus, a black tetragon, a black triangle, a black circle, a white rhombus, a white tetragon, and a white triangle represent RCP-1, RCP-11, RCP-12, RCP-13, RCP-14, RCP-15, and RCP-16, respectively.

As indicated in FIG. 1, it is found that favorable adsorptivity to a plate, equivalent to that of RCP-11 having the sequence of human vitronectin, is exhibited in a case in which among the polypeptides used in the test, the polypeptides of RCP-1, RCP-15, and RCP-16, containing PRPSLAKKQRFRHRNRKGYRSQRGHSRGRNQN (SEQ ID NO:2 [from 342nd to 373rd in SEQ ID NO:3]), are used. In contrast, it is found that the adsorption amount of RCP-13 or RCP-14 that does not contain PRPSLAKKQRFRHRN-RKGYRSQRGHSRGRNQN (SEQ ID NO:2), is as low as ¼ of that of the polypeptide containing the sequence, and RCP-13 and RCP-14 are inadequate as an adsorbent to a culture plate.

Example 3

<Cell Adhesiveness Evaluation 1>

The cell adhesiveness of human iPS cells ("Tic": cell number: No. JCRB1331: given by the National Institute of Biomedical Innovation [7-6-8 Saito-Asagi, Ibaraki-shi, Osaka 567-0085, Japan]) to the above-described polypeptides was evaluated as described below.

EMBRYOMAX (registered trademark) (primary mouse embryo fibroblasts: hygromycin resistance, mitomycin C-treated, derived from C57/BL6, third generation of subculture) (EMD Millipore Corporation) was used as feeder cells for maintaining the human iPS cells, was cultured for 24 hours using DMEM (Invitrogen) culture medium containing a 10% (v/v) fetal bovine serum, and was made to adhere onto a T25 flask (Corning Inc.). A culture medium for human iPS cells, in which FGF-2 (Sigma-Aldrich) was added to the compositions in Table 5 so as to have a final concentration of 10 ng/ml, was used.

TABLE 5

| Composition | Manufacturer | Amount |
| --- | --- | --- |
| KO-DMEM/F12 | Invitrogen | 400 ml |
| Non-Essential Amino Acid Solution | | 4 ml |
| L-Glutamine | | 5 ml |
| Knock Out Serum Replacement | | 100 ml |
| 2-Mercaptoethanol 55 mM | Wako Pure Chemical industries, Ltd. | 0.925 ml |
| | | Total: 500 ml |

The maintenance culture of the iPS cells was performed in a 5% (v/v, the same applies hereafter) $CO_2$ incubator at 37° C. using the above-described culture medium. The culture medium was replaced by a fresh culture medium every day except the next day after the seeding of the iPS cells. Subculture manipulation was performed by separating cells with DISPASE II (neutral protease GradeII, Roche) and by dividing the cells to suitable sizes by pipetting manipulation.

The human iPS cells cultured as mentioned above were treated with TRYPLE SELECT (Invitrogen) at 37° C. for 5 minutes, and were separated into single cells. The cells were collected by centrifugation at 300 rpm for 2 min, and were suspended in TESR2(component derived from a heterologous animal, serum component-free culture medium, Stem-Cell Technologies, Inc.) containing Y-27362 ((R)-(+)-trans-N-(4-pyridyl)-4-(1-aminoethyl)-cyclohexanecarboxiamide.$2HCl.H_2O$, Rho-binding kinase inhibitor, Wako Pure Chemical Industries, Ltd.) at a final concentration of 10 μM.

Samples from Ito 17 were prepared so as to have addition concentrations listed in Table 6 with from RCP-1 to RCP-10, and RCP-17, RCP-11, RCP-15, and RCP-16, and human vitronectin (extracted from human plasma, BD Biosciences) and recombinant laminin (rLaminin-5: Oriental Yeast Co., Ltd., and Human Recombinant Laminin-511: Biolamina) as references, were added to each well of a 96-well plate, were retained at 37° C. for 2 hours, and were adsorbed. iPS cells were seeded on each obtained well of the 96-well plate, which were subjected to the peptide treatment, in a manner to set a cell density of 30000 cells/ well. After culture for 24 hours, non-adherent cells were removed by PBS washing, and only the adherent cells were immobilized with 4% paraformaldehyde (Wako Pure Chemical Industries, Ltd.). ALP activity was calculated with ATTOPHOS (registered trademark) AP Fluorescent Substrate System (Promega Corporation), and the number of undifferentiated iPS cells having ALP activity was calculated from a calibration curve. The results are listed in Table 6. In Table 6, cell adhesion rates were relative values in a case in which the cell adhesion rate of the sample 15, in which the natural vitronectin was used, was regarded as 100. n=3.

TABLE 6

| | Kind of Peptide | Addition Amount | Cell Adhesion Rate (%) | Remarks |
| --- | --- | --- | --- | --- |
| Sample 1 | RCP-1 | 200 pmol/cm$^2$ | 109.3 ± 5.3 | The Invention |
| Sample 2 | RCP-2 | 20 μg/cm$^2$ | 98.7 ± 6.2 | The Invention |
| Sample 3 | RCP-3 | 20 μg/cm$^2$ | 106.1 ± 4.5 | The Invention |
| Sample 4 | RCP-4 | 20 μg/cm$^2$ | 100.1 ± 4.5 | The Invention |
| Sample 5 | RCP-5 | 10 μg/cm$^2$ | 94.1 ± 6.5 | The Invention |
| Sample 6 | RCP-6 | 20 μg/cm$^2$ | 92.8 ± 4.4 | The Invention |
| Sample 7 | RCP-7 | 5 μg/cm$^2$ | 88.6 ± 8.1 | The Invention |
| Sample 8 | RCP-8 | 5 μg/cm$^2$ | 89.2 ± 1.4 | The Invention |
| Sample 9 | RCP-9 | 20 μg/cm$^2$ | 95.5 ± 10.2 | The Invention |
| Sample 10 | RCP-10 | 20 μg/cm$^2$ | 93.0 ± 7.8 | The Invention |
| Sample 11 | RCP-17 | 5 μg/cm$^2$ | 95.9 ± 4.6 | The Invention |
| Sample 12 | RCP-11 | 200 pmol/cm$^2$ | 93.5 ± 7.9 | Comparative Example |
| Sample 13 | RCP-15 | 200 pmol/cm$^2$ | 13.2 ± 3.4 | Comparative Example |
| Sample 14 | RCP-16 | 200 pmol/cm$^2$ | 9.4 ± 2.9 | Comparative Example |
| Sample 15 | Natural vitronectin | 130 pmol/cm$^2$ | 100 ± 5.5 | Comparative Example |
| Sample 16 | rLaminin-5 | 3.2 μg/cm$^2$ | 155.7 | Comparative Example |
| Sample 17 | Laminin-511 | 5.0 μg/cm$^2$ | 142.0 | Comparative Example |

As listed in Table 6, the cell adhesion rates of iPS cells of from RCP-1 to RCP-10. RCP-17, and RCP-11, and the natural human vitronectin, having from 1st to 55th in the sequence represented by SEQ ID NO:3, were favorable. In particular, the cell adhesion rates of from RCP-1 to RCP-10, and RCP-17, which do not contain some or all of from 56th to 268th amino acids of the sequence represented by SEQ ID NO:3, were better than those of the natural human vitronectin and RCP-11 having the same amino acid sequence as that of the natural human vitronectin. This reveals that a sequence important for cell adhesion is present in from 1st to 55th in the sequence represented by SEQ ID NO:3.

Example 4

<Cell Adhesiveness Evaluation 2>

Polypeptides listed in Table 7 were synthesized by Emoc solid phase synthesis. A surface to which natural vitronectin was adsorbed at a concentration of 130 pmol/m$^2$, and thereafter, a cell suspension to which 100 μM of the above-described synthetic peptide was added was seeded at a rate of 30,000 cells/well. The number of adherent cells after 24 h post seeding was calculated by the same technique as in <Cell Adhesiveness Evaluation 1>. The results are listed in Table 7. In Table 7, the cell adhesion rates were relative values in a case in which the cell adhesion rate in a culture liquid that does not contain any synthetic peptide was regarded as 100. n=3.

TABLE 7

| Synthetic Peptide | Sequence | Cell Adhesion Rate (%) | SEQ ID NO: |
|---|---|---|---|
| Peptide-1 | DQESCKGRCTEGFNVDKKCQ | 91.8 ± 1.2 | 30 |
| Peptide-2 | KGRCTEGFNVDKKCQCDELC | 92.7 ± 19.6 | 31 |
| Peptide-3 | EGFNVDKKCQCDELCSYYQS | 102.5 ± 4.2 | 32 |
| Peptide-4 | DKKCQCDELCSYYQSCCTDY | 63.8 ± 11.6 | 33 |
| Peptide-5 | CCTDYTAECKPQVTRGDVFT | 70.5 ± 7.1 | 34 |
| Peptide-6 | TAECKPQVTRGDVFTMPEDE | 52.7 ± 10.3 | 35 |
| Peptide-7 | CCTDYTAECKPQVTRGEVFT | 86.7 ± 7.1 | 36 |
| Peptide-8 | TAECKPQVTRGEVGTMPEDE | 83.8 ± 14.8 | 37 |

As listed in Table 7, it is found that cell adhesion to natural vitronectin was significantly inhibited by adding Peptide-4, -5, or -6 containing CSYYQSC (SEQ ID NO: 1) or RGD, whereas adhesion inhibition did not occur in a case in which Peptide-1, -2, or -3, in which neither CSYYQSC (SEQ ID NO: 1) nor RGD is contained, or Peptide-7 or -8, in which the RGD sequence of Peptide-5 or -6 was substituted with RGE, was added. Accordingly, it is found that a polypeptide contains at least one of CSYYQSC (SEQ ID NO: 1) or RGD, whereby cell adhesiveness is exhibited.

Example 5

<Proliferation Evaluation>

Figure 2:
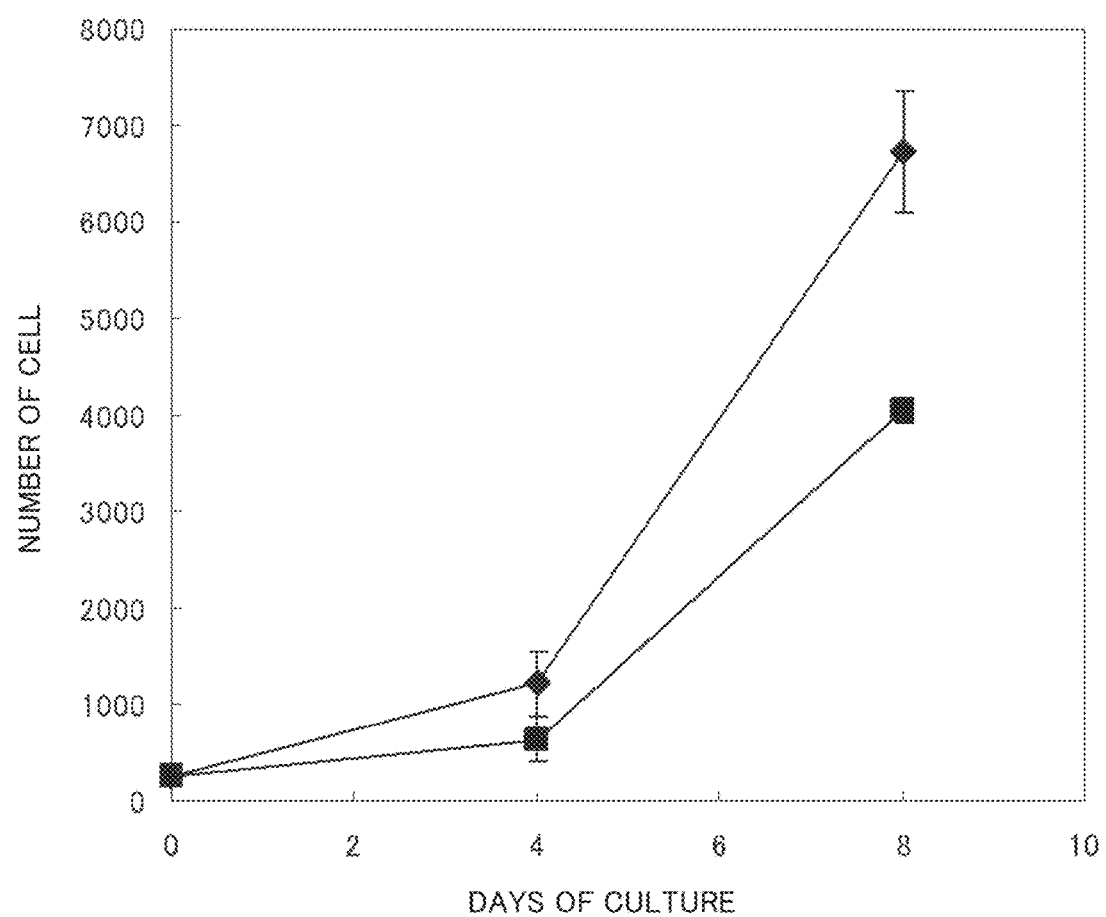
FIG. 2 is a graph indicating the proliferation curve of iPS cells using each polypeptide in Examples of the invention.
Figure 3A:
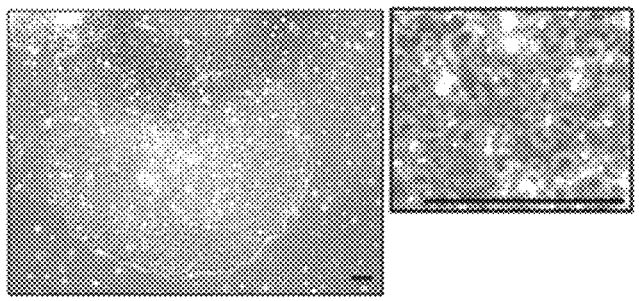
FIGS. 3A to 3E represent the morphological images (left column) and magnified images (right column) of iPS cell colonies in a case of being cultured on each polypeptide in Examples of the invention.
Figure 3B:
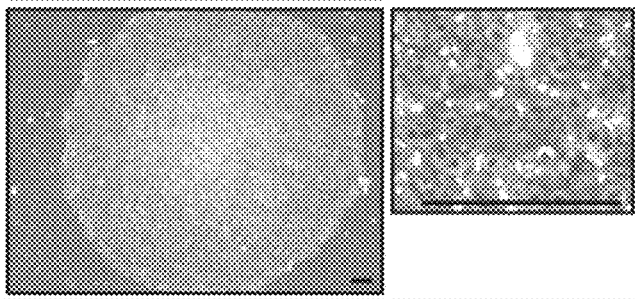
Figure 3C:
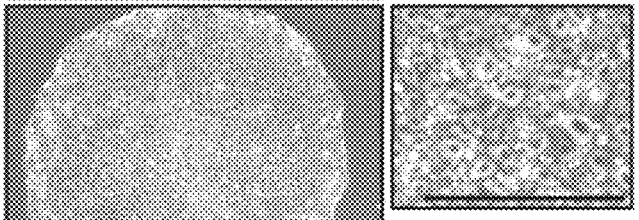
Figure 3D:
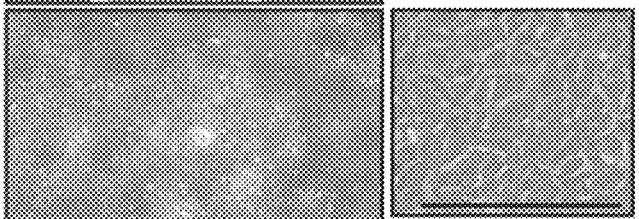
Figure 3E:
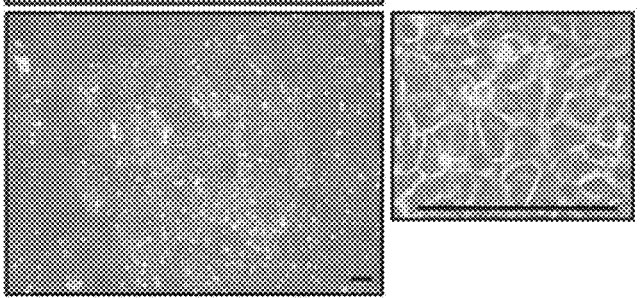
Figure 4A:
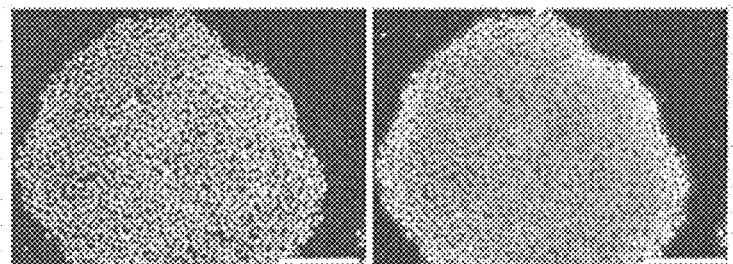
FIGS. 4A to 4E represent the images of DAPI staining (left column) and NANOG staining (right column) of iPS cells in a case of being cultured on each polypeptide in Examples of the invention.
Figure 4B:
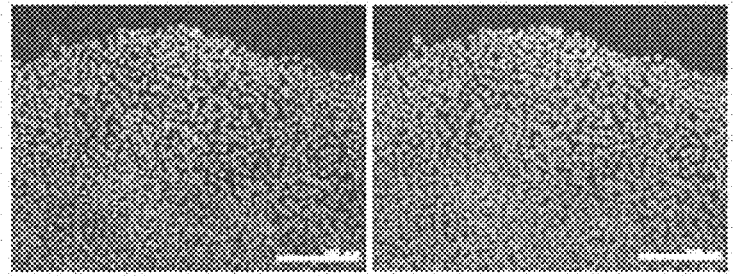
Figure 4C:
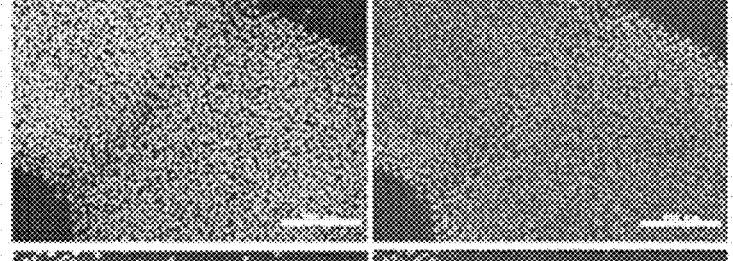
Figure 4D:
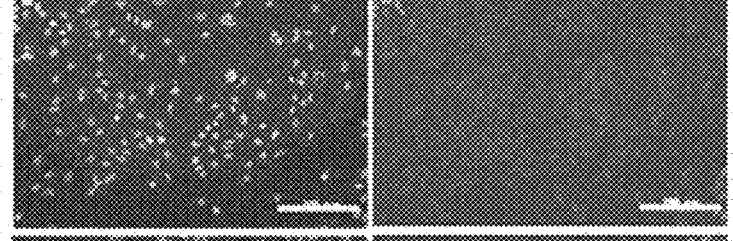
Figure 4E:
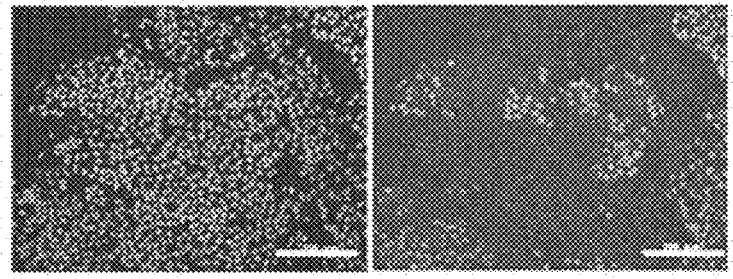

The iPS cells collected in the same manner as in <Cell Adhesiveness Evaluation 1>described above were seeded on a 96-well plate, to which RCP-1, RCP-11, and the natural human vitronectin were adsorbed, at a rate of 250 cells/well, and were cultured in a 5% $CO_2$ incubator at 37° C. for 8 days. The number of adherent cells after each lapse of time was measured by the same method as in <Cell Adhesiveness Evaluation 1> described above, to obtain proliferation curves, The proliferation curves were indicated in FIG. 2. In FIG. 2, a black rhombus represents an example in which RCP-1 was used, while a black tetragon represents an example in which RCP-11 was used.

Similarly, each of samples from Ito 12 was prepared so as to have an addition concentration listed in Table 8 with each of from RCP-1 to RCP-10, and RCP-17, and Human Recombinant Laminin-511 as a reference, was seeded on a 96-well plate, to which each polypeptide was adsorbed, at a rate of 5000 cells/well in the same manner as in<Cell Adhesiveness Evaluation 1> described above, and was cultured in a $CO_2$ incubator at 37° C. for 3 days. The number of cells after the 3 days was measured by the same method as in <Cell Adhesiveness Evaluation 1> described above. The results are listed in Table 8.

TABLE 8

| | Kind of Peptide | Addition Amount | The Number (%) of Cells after 3 Days | Remarks |
|---|---|---|---|---|
| Sample 1 | RCP-1 | 80 µg/cm² | 100.0 | The Invention |
| Sample 2 | RCP-2 | 20 µg/cm² | 81.7 | The Invention |
| Sample 3 | RCP-3 | 20 µg/cm² | 109.7 | The Invention |
| Sample 4 | RCP-4 | 20 µg/cm² | 120.7 | The Invention |
| Sample 5 | RCP-5 | 10 µg/cm² | 121.2 | The Invention |
| Sample 6 | RCP-6 | 20 µg/cm² | 70.5 | The Invention |
| Sample 7 | RCP-7 | 5 µg/cm² | 89.9 | The Invention |
| Sample 8 | RCP-8 | 5 µg/cm² | 171.0 | The Invention |
| Sample 9 | RCP-9 | 20 µg/cm² | 105.8 | The Invention |
| Sample 10 | RCP-10 | 20 µg/cm² | 101.9 | The Invention |
| Sample 11 | RCP-17 | 5 µg/cm² | 153.5 | The Invention |
| Sample 12 | Laminin-511 | 1.28 µg/cm² | 56.8 | Comparative Example |

FIG. 2 reveals that RCP-1 exhibited a higher cell proliferation property than that of RCP-11 having the amino acid sequence of natural vitronectin. The number of cells of RCP-11 was smaller than that of RCP-1 by around ⅓ of that of RCP-1 on culture day 8. It was calculated from the change of each obtained cell number that doubling time was 46.4±2.1 hours in the case of using RCP-1, and that was 67.7±2.1 hours in a case of using RCP-11.

In addition, Table 8 reveals that all of from RCP-1 to RCP-10, and RCP-17 have higher cell proliferation rates than that of laminin, which is an extracellular matrix similarly to vitronectin. It is found that such a high cell proliferation rate is also obtained in the similar manner in a case in which the 274th cysteine residue in SEQ ED NO:3 is substituted with a serine residue.

The results of FIG. 2 and Table 8 surprisingly reveal that from RCP-1 to RCP-10, and RCP-17, which include the sequences effective for cell proliferation and adsorption to a culture plate and do not contain any sequence corresponding to any or all of from the 56th to 268th amino acids of natural human vitronectin, have higher proliferation potencies than RCP-11 having the sequence equivalent to that of the human vitronectin, and Laminin-511 as a comparative example.

In addition, Table 8 reveals that all of from RCP-1 to RCP-10, and RCP-17, containing both of the sequence of CSYYQSC and the RGD sequence, and the sequence of PRPSLAKKQRFRHRNRKGYRSQRGHSRGRNQN (SEQ ID NO: 2) exhibited high cell proliferation properties.

Example 6

<Cell Adhesiveness Evaluation 3>

Cell adhesiveness was evaluated in the same manner as in <Cell Adhesiveness Evaluation 1> except that RCP-1 was adjusted with PBS to have a concentration of from 125 pmol/cm² to 1000 pmol/cm² to be used. The results are listed in Table 9. In Table 9, cell adhesion rates were relative values in a case in which a cell adhesion rate to a cultivation container to which natural vitronectin was adsorbed at a concentration of 130 pmol/cm² was regarded as 100. n=3.

TABLE 9

| Peptide | Addition Amount | Cell Adhesion Rate (%) | Remarks |
|---|---|---|---|
| RCP-1 | 1000 pmol/cm² | 98.5 ± 17.2 | The Invention |
| RCP-1 | 500 pmol/cm² | 108.8 ± 23.0 | The Invention |
| RCP-1 | 250 pmol/cm² | 89.2 ± 10.6 | The Invention |
| RCP-1 | 125 pmol/cm² | 90.3 ± 25.3 | The Invention |
| Natural vitronectin | 130 pmol/cm² | 100 ± 5.5 | Comparative Example |

As listed in Table 9, as for the adhesiveness of iPS cells to RCP-1, a cell adhesion rate equivalent to that of natural vitronectin was exhibited in a case of adding not less than 125 pmol/cm².

Example 7

<Evaluation of Maintenance of Undifferentiation> iPS cells collected in the same manner as in <Cell Adhesiveness Evaluation 1> described above were suspended in TESR2. Induced pluripotent stem cells (iPS cells) were seeded on a 6-well plate (Tissue Culture-Treated, Falcon) to which each of the sample 1, the sample 2, the sample 5, the sample 6, and the sample 7 used in <Cell Adhesiveness Evaluation 1> described above was adsorbed in the same manner as in <Cell Adhesiveness Evaluation 1>, and were cultured in a $CO_2$ incubator at 37° C. The culture medium was replaced by a fresh culture medium every day except the next day after the seeding. Subculture was performed by the same method as mentioned above every six days. The forms of the iPS cells cultured on each sample are shown in FIG. 3.

The cells were cultured under these conditions for 1 month, thereafter immobilized with 4% paraformaldehyde, and made to have membrane permeability enhanced with 1% Triton-X/PBS. Blocking treatment was performed with an Image IT Signal Enhancer (Invitrogen), followed by adding an anti-human NANOG antibody (AF1997, R&D Systems, Inc), ALEXA FLUOR 555-CONJUGATE rabbit anti-goat IgG antibody (Invitrogen), and DAPI (Dojindo Laboratories), by performing labeling, and by photographing the cells with a fluorescence microscope. These fluorescence microscope images are shown in FIG. 4.

In each of FIG. 3 and FIG. 4, "A", "B", "C" "D", and "E" show iPS cells cultured on RCP-1, iPS cells cultured on RCP-11, iPS cells cultured on the natural human vitronectin, iPS cells cultured on rinaminin-5, and iPS cells cultured on rLaminin-511, respectively. Scale bar: 100 μm. In FIG. 3, overall colony images are shown in the left column, while magnified images are shown in the right column; and in FIG. 4, DAPI-stained images are shown in the left column while anti-NANOG antibody-stained images are shown in the right column. Scale bars in FIGS. 3 and 4: 200 μm.

As shown in FIG. 3, the iPS cells cultured on RCP-1, RCP-11, or natural human vitronectin, which contains the sequence effective for cell proliferation and adsorption to a culture plate, exhibited a homogeneous colony and a form characteristic for undifferentiated cells having a high nucleus occupying rate. As shown in FIG. 4, the iPS cells cultured on RCP-1, RCP-11, or natural human vitronectin having a cell proliferation domain and an adsorption domain strongly expressed NANOG in an overall colony, and it was found that an undifferentiated state was favorably maintained.

The evaluation results of the above-described examples from 1 to 7 reveal that the polypeptide containing either of CSYYQSC (SEQ ID NO: 1) or the RGD sequence, and the sequence of PRPSLAKKQRFRHRNRKGYRSQRGHSR-GRNQN (SEQ ID NO: 2), and consisting of from 40 to 450 amino acid residues was excellent in adsorptivity to a cultivation container. The results also reveal that under conditions of cocultivation with iPS cells, such a polypeptide exhibited the cell adhesiveness of the iPS cell, and the maintenance of an undifferentiated state which are equivalent to those of RCP-11 having the sequence equivalent to those of the natural vitronectin and human vitronectin, and the properties of proliferation of the iPS cells which is superior to that of RCP-11. It is found that all of from RCP-1 to RCP-10, and RCP-17 are favorable in view of the cell adhesiveness of iPS cells and the maintenance of an undifferentiated state. Such favorable results in all the abilities were not able to be obtained in the other polypeptides or the recombinant laminin as the comparative example.

Accordingly, the invention can provide a polypeptide that enables a pluripotent stem cell to proliferate in an undifferentiated state and is excellent in adsorptivity to a cell culture surface, a method of culturing a pluripotent stem cell using the polypeptide, and a cultivation container.

The disclosure of Japanese Patent Application No. 2012-104816, filed on May 1, 2012, is incorporated herein by reference in its entirety.

All the literature, patent applications, and technical standards described herein are herein incorporated by reference to the same extent as if each individual literature, patent application, or technical standard was specifically and individually indicated as being incorporated by reference.

What is claimed is:

1. A polypeptide comprising an amino acid sequence represented by any of SEQ ID NO:4 to SEQ ID NO:23, SEQ ID NO:38, or SEQ ID NO:39.

2. A method of culturing a pluripotent stem cell, comprising:
    applying the polypeptide according to claim 1 to a cell culture surface of a support, to obtain a polypeptide-coated culture surface; and
    seeding a pluripotent stem cell on the polypeptide-coated culture surface and culturing the pluripotent stem cell.

3. The method of culturing a pluripotent stem cell according to claim 2, wherein the pluripotent stem cell is at least one selected from the group consisting of embryonic stem cells, induced pluripotent stem cells, somatic stem cells, fertilized egg inner cell mass cells, and early embryonic cells.

4. The method of culturing a pluripotent stem cell according to claim 2, wherein the pluripotent stem cell is cultured in the absence of a component obtained from a heterologous animal and a component obtained from serum.

* * * * *

SEQUENCE LISTING

```
<160> NUMBER OF SEQ ID NOS: 43

<210> SEQ ID NO 1
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 1

Cys Ser Tyr Tyr Gln Ser Cys
1               5
```

-continued

```
<210> SEQ ID NO 2
<211> LENGTH: 32
<212> TYPE: PRT
<213> ORGANISM: Artificial Sequence
<220> FEATURE:
<223> OTHER INFORMATION: Synthetic Heparin Binding Domain

<400> SEQUENCE: 2

Pro Arg Pro Ser Leu Ala Lys Lys Gln Arg Phe Arg His Arg Asn Arg
1               5                   10                  15

Lys Gly Tyr Arg Ser Gln Arg Gly His Ser Arg Gly Arg Asn Gln Asn
            20                  25                  30

<210> SEQ ID NO 3
<211> LENGTH: 459
<212> TYPE: PRT
<213> ORGANISM: Homo sapiens

<400> SEQUENCE: 3

Asp Gln Glu Ser Cys Lys Gly Arg Cys Thr Glu Gly Phe Asn Val Asp
1               5                   10                  15

Lys Lys Cys Gln Cys Asp Glu Leu Cys Ser Tyr Tyr Gln Ser Cys Cys
            20                  25                  30

Thr Asp Tyr Thr Ala Glu Cys Lys Pro Gln Val Thr Arg Gly Asp Val
        35                  40                  45

Phe Thr Met Pro Glu Asp Glu Tyr Thr Val Tyr Asp Asp Gly Glu Glu
    50                  55                  60

Lys Asn Asn Ala Thr Val His Glu Gln Val Gly Gly Pro Ser Leu Thr
65                  70                  75                  80

Ser Asp Leu Gln Ala Gln Ser Lys Gly Asn Pro Glu Gln Thr Pro Val
                85                  90                  95

Leu Lys Pro Glu Glu Glu Ala Pro Ala Pro Glu Val Gly Ala Ser Lys
            100                 105                 110

Pro Glu Gly Ile Asp Ser Arg Pro Glu Thr Leu His Pro Gly Arg Pro
        115                 120                 125

Gln Pro Pro Ala Glu Glu Glu Leu Cys Ser Gly Lys Pro Phe Asp Ala
    130                 135                 140

Phe Thr Asp Leu Lys Asn Gly Ser Leu Phe Ala Phe Arg Gly Gln Tyr
145                 150                 155                 160

Cys Tyr Glu Leu Asp Glu Lys Ala Val Arg Pro Gly Tyr Pro Lys Leu
                165                 170                 175

Ile Arg Asp Val Trp Gly Ile Glu Gly Pro Ile Asp Ala Ala Phe Thr
            180                 185                 190

Arg Ile Asn Cys Gln Gly Lys Thr Tyr Leu Phe Lys Gly Ser Gln Tyr
        195                 200                 205

Trp Arg Phe Glu Asp Gly Val Leu Asp Pro Asp Tyr Pro Arg Asn Ile
    210                 215                 220

Ser Asp Gly Phe Asp Gly Ile Pro Asp Asn Val Asp Ala Ala Leu Ala
225                 230                 235                 240

Leu Pro Ala His Ser Tyr Ser Gly Arg Glu Arg Val Tyr Phe Phe Lys
                245                 250                 255

Gly Lys Gln Tyr Trp Glu Tyr Gln Phe Gln His Gln Pro Ser Gln Glu
            260                 265                 270

Glu Cys Glu Gly Ser Ser Leu Ser Ala Val Phe Glu His Phe Ala Met
        275                 280                 285

Met Gln Arg Asp Ser Trp Glu Asp Ile Phe Glu Leu Leu Phe Trp Gly
    290                 295                 300
```

Arg Thr Ser Ala Gly Thr Arg Gln Pro Gln Phe Ile Ser Arg Asp Trp
305                 310                 315                 320

His Gly Val Pro Gly Gln Val Asp Ala Ala Met Ala Gly Arg Ile Tyr
            325                 330                 335

Ile Ser Gly Met Ala Pro Arg Pro Ser Leu Ala Lys Lys Gln Arg Phe
        340                 345                 350

Arg His Arg Asn Arg Lys Gly Tyr Arg Ser Gln Arg Gly His Ser Arg
    355                 360                 365

Gly Arg Asn Gln Asn Ser Arg Arg Pro Ser Arg Ala Thr Trp Leu Ser
370                 375                 380

Leu Phe Ser Ser Glu Glu Ser Asn Leu Gly Ala Asn Asn Tyr Asp Asp
385                 390                 395                 400

Tyr Arg Met Asp Trp Leu Val Pro Ala Thr Cys Glu Pro Ile Gln Ser
            405                 410                 415

Val Phe Phe Phe Ser Gly Asp Lys Tyr Tyr Arg Val Asn Leu Arg Thr
        420                 425                 430

Arg Arg Val Asp Thr Val Asp Pro Pro Tyr Pro Arg Ser Ile Ala Gln
    435                 440                 445

Tyr Trp Leu Gly Cys Pro Ala Pro Gly His Leu
450                 455

<210> SEQ ID NO 4
<211> LENGTH: 246
<212> TYPE: PRT
<213> ORGANISM: Artificial Sequence
<220> FEATURE:
<223> OTHER INFORMATION: Synthetic Peptide

<400> SEQUENCE: 4

Asp Gln Glu Ser Cys Lys Gly Arg Cys Thr Glu Gly Phe Asn Val Asp
1               5                   10                  15

Lys Lys Cys Gln Cys Asp Glu Leu Cys Ser Tyr Tyr Gln Ser Cys Cys
            20                  25                  30

Thr Asp Tyr Thr Ala Glu Cys Lys Pro Gln Val Thr Arg Gly Asp Val
        35                  40                  45

Phe Thr Met Pro Glu Asp Glu Pro Ser Gln Glu Glu Cys Glu Gly Ser
    50                  55                  60

Ser Leu Ser Ala Val Phe Glu His Phe Ala Met Met Gln Arg Asp Ser
65                  70                  75                  80

Trp Glu Asp Ile Phe Glu Leu Leu Phe Trp Gly Arg Thr Ser Ala Gly
            85                  90                  95

Thr Arg Gln Pro Gln Phe Ile Ser Arg Asp Trp His Gly Val Pro Gly
        100                 105                 110

Gln Val Asp Ala Ala Met Ala Gly Arg Ile Tyr Ile Ser Gly Met Ala
    115                 120                 125

Pro Arg Pro Ser Leu Ala Lys Lys Gln Arg Phe Arg His Arg Asn Arg
130                 135                 140

Lys Gly Tyr Arg Ser Gln Arg Gly His Ser Arg Gly Arg Asn Gln Asn
145                 150                 155                 160

Ser Arg Arg Pro Ser Arg Ala Thr Trp Leu Ser Leu Phe Ser Ser Glu
            165                 170                 175

Glu Ser Asn Leu Gly Ala Asn Asn Tyr Asp Asp Tyr Arg Met Asp Trp
        180                 185                 190

Leu Val Pro Ala Thr Cys Glu Pro Ile Gln Ser Val Phe Phe Phe Ser
    195                 200                 205

```
Gly Asp Lys Tyr Tyr Arg Val Asn Leu Arg Thr Arg Val Asp Thr
    210                 215                 220
Val Asp Pro Pro Tyr Pro Arg Ser Ile Ala Gln Tyr Trp Leu Gly Cys
225                 230                 235                 240
Pro Ala Pro Gly His Leu
                245
```

<210> SEQ ID NO 5
<211> LENGTH: 87
<212> TYPE: PRT
<213> ORGANISM: Artificial Sequence
<220> FEATURE:
<223> OTHER INFORMATION: Synthetic Peptide

<400> SEQUENCE: 5

```
Asp Gln Glu Ser Cys Lys Gly Arg Cys Thr Glu Gly Phe Asn Val Asp
1               5                   10                  15
Lys Lys Cys Gln Cys Asp Glu Leu Cys Ser Tyr Tyr Gln Ser Cys Cys
                20                  25                  30
Thr Asp Tyr Thr Ala Glu Cys Lys Pro Gln Val Thr Arg Gly Asp Val
            35                  40                  45
Phe Thr Met Pro Glu Asp Glu Pro Arg Pro Ser Leu Ala Lys Lys Gln
        50                  55                  60
Arg Phe Arg His Arg Asn Arg Lys Gly Tyr Arg Ser Gln Arg Gly His
65                  70                  75                  80
Ser Arg Gly Arg Asn Gln Asn
                85
```

<210> SEQ ID NO 6
<211> LENGTH: 107
<212> TYPE: PRT
<213> ORGANISM: Artificial Sequence
<220> FEATURE:
<223> OTHER INFORMATION: Synthetic Peptide

<400> SEQUENCE: 6

```
Asp Gln Glu Ser Cys Lys Gly Arg Cys Thr Glu Gly Phe Asn Val Asp
1               5                   10                  15
Lys Lys Cys Gln Cys Asp Glu Leu Cys Ser Tyr Tyr Gln Ser Cys Cys
                20                  25                  30
Thr Asp Tyr Thr Ala Glu Cys Lys Pro Gln Val Thr Arg Gly Asp Val
            35                  40                  45
Phe Thr Met Pro Glu Asp Glu Gly Val Pro Gly Gln Val Asp Ala Ala
        50                  55                  60
Met Ala Gly Arg Ile Tyr Ile Ser Gly Met Ala Pro Arg Pro Ser Leu
65                  70                  75                  80
Ala Lys Lys Gln Arg Phe Arg His Arg Asn Arg Lys Gly Tyr Arg Ser
                85                  90                  95
Gln Arg Gly His Ser Arg Gly Arg Asn Gln Asn
            100                 105
```

<210> SEQ ID NO 7
<211> LENGTH: 117
<212> TYPE: PRT
<213> ORGANISM: Artificial Sequence
<220> FEATURE:
<223> OTHER INFORMATION: Synthetic Peptide

<400> SEQUENCE: 7

```
Asp Gln Glu Ser Cys Lys Gly Arg Cys Thr Glu Gly Phe Asn Val Asp
1               5                   10                  15

Lys Lys Cys Gln Cys Asp Glu Leu Cys Ser Tyr Tyr Gln Ser Cys Cys
            20                  25                  30

Thr Asp Tyr Thr Ala Glu Cys Lys Pro Gln Val Thr Arg Gly Asp Val
        35                  40                  45

Phe Thr Met Pro Glu Asp Glu Gln Pro Gln Phe Ile Ser Arg Asp Trp
    50                  55                  60

His Gly Val Pro Gly Gln Val Asp Ala Ala Met Ala Gly Arg Ile Tyr
65                  70                  75                  80

Ile Ser Gly Met Ala Pro Arg Pro Ser Leu Ala Lys Lys Gln Arg Phe
            85                  90                  95

Arg His Arg Asn Arg Lys Gly Tyr Arg Ser Gln Arg Gly His Ser Arg
            100                 105                 110

Gly Arg Asn Gln Asn
            115

<210> SEQ ID NO 8
<211> LENGTH: 127
<212> TYPE: PRT
<213> ORGANISM: Artificial Sequence
<220> FEATURE:
<223> OTHER INFORMATION: Synthetic Peptide

<400> SEQUENCE: 8

Asp Gln Glu Ser Cys Lys Gly Arg Cys Thr Glu Gly Phe Asn Val Asp
1               5                   10                  15

Lys Lys Cys Gln Cys Asp Glu Leu Cys Ser Tyr Tyr Gln Ser Cys Cys
            20                  25                  30

Thr Asp Tyr Thr Ala Glu Cys Lys Pro Gln Val Thr Arg Gly Asp Val
        35                  40                  45

Phe Thr Met Pro Glu Asp Glu Phe Trp Gly Arg Thr Ser Ala Gly Thr
    50                  55                  60

Arg Gln Pro Gln Phe Ile Ser Arg Asp Trp His Gly Val Pro Gly Gln
65                  70                  75                  80

Val Asp Ala Ala Met Ala Gly Arg Ile Tyr Ile Ser Gly Met Ala Pro
            85                  90                  95

Arg Pro Ser Leu Ala Lys Lys Gln Arg Phe Arg His Arg Asn Arg Lys
            100                 105                 110

Gly Tyr Arg Ser Gln Arg Gly His Ser Arg Gly Arg Asn Gln Asn
            115                 120                 125

<210> SEQ ID NO 9
<211> LENGTH: 245
<212> TYPE: PRT
<213> ORGANISM: Artificial Sequence
<220> FEATURE:
<223> OTHER INFORMATION: Synthetic Peptide

<400> SEQUENCE: 9

Asp Gln Glu Ser Cys Lys Gly Arg Cys Thr Glu Gly Phe Asn Val Asp
1               5                   10                  15

Lys Lys Cys Gln Cys Asp Glu Leu Cys Ser Tyr Tyr Gln Ser Cys Cys
            20                  25                  30

Thr Asp Tyr Thr Ala Glu Cys Lys Pro Gln Val Thr Arg Gly Asp Val
        35                  40                  45

Phe Thr Met Pro Glu Asp Glu Ser Gln Glu Glu Ser Glu Gly Ser Ser
    50                  55                  60
```

```
Leu Ser Ala Val Phe Glu His Phe Ala Met Met Gln Arg Asp Ser Trp
 65                  70                  75                  80

Glu Asp Ile Phe Glu Leu Leu Phe Trp Gly Arg Thr Ser Ala Gly Thr
                 85                  90                  95

Arg Gln Pro Gln Phe Ile Ser Arg Asp Trp His Gly Val Pro Gly Gln
            100                 105                 110

Val Asp Ala Ala Met Ala Gly Arg Ile Tyr Ile Ser Gly Met Ala Pro
            115                 120                 125

Arg Pro Ser Leu Ala Lys Lys Gln Arg Phe Arg His Arg Asn Arg Lys
130                 135                 140

Gly Tyr Arg Ser Gln Arg Gly His Ser Arg Gly Arg Asn Gln Asn Ser
145                 150                 155                 160

Arg Arg Pro Ser Arg Ala Thr Trp Leu Ser Leu Phe Ser Ser Glu Glu
                165                 170                 175

Ser Asn Leu Gly Ala Asn Asn Tyr Asp Asp Tyr Arg Met Asp Trp Leu
            180                 185                 190

Val Pro Ala Thr Ser Glu Pro Ile Gln Ser Val Phe Phe Ser Gly
            195                 200                 205

Asp Lys Tyr Tyr Arg Val Asn Leu Arg Thr Arg Val Asp Thr Val
210                 215                 220

Asp Pro Pro Tyr Pro Arg Ser Ile Ala Gln Tyr Trp Leu Gly Ser Pro
225                 230                 235                 240

Ala Pro Gly His Leu
            245

<210> SEQ ID NO 10
<211> LENGTH: 159
<212> TYPE: PRT
<213> ORGANISM: Artificial Sequence
<220> FEATURE:
<223> OTHER INFORMATION: Synthetic Peptide

<400> SEQUENCE: 10

Asp Gln Glu Ser Cys Lys Gly Arg Cys Thr Glu Gly Phe Asn Val Asp
 1               5                  10                  15

Lys Lys Cys Gln Cys Asp Glu Leu Cys Ser Tyr Tyr Gln Ser Cys Cys
                20                  25                  30

Thr Asp Tyr Thr Ala Glu Cys Lys Pro Gln Val Thr Arg Gly Asp Val
            35                  40                  45

Phe Thr Met Pro Glu Asp Glu Ser Gln Glu Glu Ser Glu Gly Ser Ser
 50                  55                  60

Leu Ser Ala Val Phe Glu His Phe Ala Met Met Gln Arg Asp Ser Trp
 65                  70                  75                  80

Glu Asp Ile Phe Glu Leu Leu Phe Trp Gly Arg Thr Ser Ala Gly Thr
                 85                  90                  95

Arg Gln Pro Gln Phe Ile Ser Arg Asp Trp His Gly Val Pro Gly Gln
            100                 105                 110

Val Asp Ala Ala Met Ala Gly Arg Ile Tyr Ile Ser Gly Met Ala Pro
            115                 120                 125

Arg Pro Ser Leu Ala Lys Lys Gln Arg Phe Arg His Arg Asn Arg Lys
130                 135                 140

Gly Tyr Arg Ser Gln Arg Gly His Ser Arg Gly Arg Asn Gln Asn
145                 150                 155

<210> SEQ ID NO 11
```

```
<211> LENGTH: 165
<212> TYPE: PRT
<213> ORGANISM: Artificial Sequence
<220> FEATURE:
<223> OTHER INFORMATION: Synthetic Peptide

<400> SEQUENCE: 11

Asp Gln Glu Ser Cys Lys Gly Arg Cys Thr Glu Gly Phe Asn Val Asp
1               5                   10                  15

Lys Lys Cys Gln Cys Asp Glu Leu Cys Ser Tyr Tyr Gln Ser Cys Cys
                20                  25                  30

Thr Asp Tyr Thr Ala Glu Cys Lys Pro Gln Val Thr Arg Gly Asp Val
            35                  40                  45

Phe Thr Met Pro Glu Asp Glu Ser Gln Glu Glu Ser Glu Gly Ser Ser
    50                  55                  60

Leu Ser Ala Val Phe Glu His Phe Ala Met Met Gln Arg Asp Ser Trp
65                  70                  75                  80

Glu Asp Ile Phe Glu Leu Leu Phe Trp Gly Arg Thr Ser Ala Gly Thr
                85                  90                  95

Arg Gln Pro Gln Phe Ile Ser Arg Asp Trp His Gly Val Pro Gly Gln
            100                 105                 110

Val Asp Ala Ala Met Ala Gly Arg Ile Tyr Ile Ser Gly Met Ala Pro
        115                 120                 125

Arg Pro Ser Leu Ala Lys Lys Gln Arg Phe Arg His Arg Asn Arg Lys
    130                 135                 140

Gly Tyr Arg Ser Gln Arg Gly His Ser Arg Gly Arg Asn Gln Asn Ser
145                 150                 155                 160

Arg Arg Pro Ser Arg
                165

<210> SEQ ID NO 12
<211> LENGTH: 175
<212> TYPE: PRT
<213> ORGANISM: Artificial Sequence
<220> FEATURE:
<223> OTHER INFORMATION: Synthetic Peptide

<400> SEQUENCE: 12

Asp Gln Glu Ser Cys Lys Gly Arg Cys Thr Glu Gly Phe Asn Val Asp
1               5                   10                  15

Lys Lys Cys Gln Cys Asp Glu Leu Cys Ser Tyr Tyr Gln Ser Cys Cys
                20                  25                  30

Thr Asp Tyr Thr Ala Glu Cys Lys Pro Gln Val Thr Arg Gly Asp Val
            35                  40                  45

Phe Thr Met Pro Glu Asp Glu Ser Gln Glu Glu Ser Glu Gly Ser Ser
    50                  55                  60

Leu Ser Ala Val Phe Glu His Phe Ala Met Met Gln Arg Asp Ser Trp
65                  70                  75                  80

Glu Asp Ile Phe Glu Leu Leu Phe Trp Gly Arg Thr Ser Ala Gly Thr
                85                  90                  95

Arg Gln Pro Gln Phe Ile Ser Arg Asp Trp His Gly Val Pro Gly Gln
            100                 105                 110

Val Asp Ala Ala Met Ala Gly Arg Ile Tyr Ile Ser Gly Met Ala Pro
        115                 120                 125

Arg Pro Ser Leu Ala Lys Lys Gln Arg Phe Arg His Arg Asn Arg Lys
    130                 135                 140

Gly Tyr Arg Ser Gln Arg Gly His Ser Arg Gly Arg Asn Gln Asn Ser
```

```
                145                 150                 155                 160
Arg Arg Pro Ser Arg Ala Thr Trp Leu Ser Leu Phe Ser Ser Glu
                165                 170                 175

<210> SEQ ID NO 13
<211> LENGTH: 185
<212> TYPE: PRT
<213> ORGANISM: Artificial Sequence
<220> FEATURE:
<223> OTHER INFORMATION: Synthetic Peptide

<400> SEQUENCE: 13

Asp Gln Glu Ser Cys Lys Gly Arg Cys Thr Glu Gly Phe Asn Val Asp
1               5                   10                  15

Lys Lys Cys Gln Cys Asp Glu Leu Cys Ser Tyr Tyr Gln Ser Cys Cys
                20                  25                  30

Thr Asp Tyr Thr Ala Glu Cys Lys Pro Gln Val Thr Arg Gly Asp Val
            35                  40                  45

Phe Thr Met Pro Glu Asp Glu Ser Gln Glu Ser Glu Gly Ser Ser
        50                  55                  60

Leu Ser Ala Val Phe Glu His Phe Ala Met Met Gln Arg Asp Ser Trp
65                  70                  75                  80

Glu Asp Ile Phe Glu Leu Leu Phe Trp Gly Arg Thr Ser Ala Gly Thr
                85                  90                  95

Arg Gln Pro Gln Phe Ile Ser Arg Asp Trp His Gly Val Pro Gly Gln
                100                 105                 110

Val Asp Ala Ala Met Ala Gly Arg Ile Tyr Ile Ser Gly Met Ala Pro
            115                 120                 125

Arg Pro Ser Leu Ala Lys Lys Gln Arg Phe Arg His Arg Asn Arg Lys
130                 135                 140

Gly Tyr Arg Ser Gln Arg Gly His Ser Arg Gly Arg Asn Gln Asn Ser
145                 150                 155                 160

Arg Arg Pro Ser Arg Ala Thr Trp Leu Ser Leu Phe Ser Ser Glu Glu
                165                 170                 175

Ser Asn Leu Gly Ala Asn Asn Tyr Asp
            180                 185

<210> SEQ ID NO 14
<211> LENGTH: 247
<212> TYPE: PRT
<213> ORGANISM: Artificial Sequence
<220> FEATURE:
<223> OTHER INFORMATION: Synthetic Peptide RCP-1

<400> SEQUENCE: 14

Met Asp Gln Glu Ser Cys Lys Gly Arg Cys Thr Glu Gly Phe Asn Val
1               5                   10                  15

Asp Lys Lys Cys Gln Cys Asp Glu Leu Cys Ser Tyr Tyr Gln Ser Cys
                20                  25                  30

Cys Thr Asp Tyr Thr Ala Glu Cys Lys Pro Gln Val Thr Arg Gly Asp
            35                  40                  45

Val Phe Thr Met Pro Glu Asp Glu Pro Ser Gln Glu Glu Cys Glu Gly
        50                  55                  60

Ser Ser Leu Ser Ala Val Phe Glu His Phe Ala Met Met Gln Arg Asp
65                  70                  75                  80

Ser Trp Glu Asp Ile Phe Glu Leu Leu Phe Trp Gly Arg Thr Ser Ala
                85                  90                  95
```

-continued

Gly Thr Arg Gln Pro Gln Phe Ile Ser Arg Asp Trp His Gly Val Pro
            100                 105                 110

Gly Gln Val Asp Ala Ala Met Ala Gly Arg Ile Tyr Ile Ser Gly Met
        115                 120                 125

Ala Pro Arg Pro Ser Leu Ala Lys Lys Gln Arg Phe Arg His Arg Asn
    130                 135                 140

Arg Lys Gly Tyr Arg Ser Gln Arg Gly His Ser Arg Gly Arg Asn Gln
145                 150                 155                 160

Asn Ser Arg Arg Pro Ser Arg Ala Thr Trp Leu Ser Leu Phe Ser Ser
                165                 170                 175

Glu Glu Ser Asn Leu Gly Ala Asn Asn Tyr Asp Asp Tyr Arg Met Asp
            180                 185                 190

Trp Leu Val Pro Ala Thr Cys Glu Pro Ile Gln Ser Val Phe Phe Phe
        195                 200                 205

Ser Gly Asp Lys Tyr Tyr Arg Val Asn Leu Arg Thr Arg Arg Val Asp
    210                 215                 220

Thr Val Asp Pro Pro Tyr Pro Arg Ser Ile Ala Gln Tyr Trp Leu Gly
225                 230                 235                 240

Cys Pro Ala Pro Gly His Leu
                245

<210> SEQ ID NO 15
<211> LENGTH: 88
<212> TYPE: PRT
<213> ORGANISM: Artificial Sequence
<220> FEATURE:
<223> OTHER INFORMATION: Synthetic Peptide RCP-2

<400> SEQUENCE: 15

Met Asp Gln Glu Ser Cys Lys Gly Arg Cys Thr Glu Gly Phe Asn Val
1               5                   10                  15

Asp Lys Lys Cys Gln Cys Asp Glu Leu Cys Ser Tyr Tyr Gln Ser Cys
            20                  25                  30

Cys Thr Asp Tyr Thr Ala Glu Cys Lys Pro Gln Val Thr Arg Gly Asp
        35                  40                  45

Val Phe Thr Met Pro Glu Asp Glu Pro Arg Pro Ser Leu Ala Lys Lys
    50                  55                  60

Gln Arg Phe Arg His Arg Asn Arg Lys Gly Tyr Arg Ser Gln Arg Gly
65                  70                  75                  80

His Ser Arg Gly Arg Asn Gln Asn
                85

<210> SEQ ID NO 16
<211> LENGTH: 108
<212> TYPE: PRT
<213> ORGANISM: Artificial Sequence
<220> FEATURE:
<223> OTHER INFORMATION: Synthetic Peptide RCP-3

<400> SEQUENCE: 16

Met Asp Gln Glu Ser Cys Lys Gly Arg Cys Thr Glu Gly Phe Asn Val
1               5                   10                  15

Asp Lys Lys Cys Gln Cys Asp Glu Leu Cys Ser Tyr Tyr Gln Ser Cys
            20                  25                  30

Cys Thr Asp Tyr Thr Ala Glu Cys Lys Pro Gln Val Thr Arg Gly Asp
        35                  40                  45

Val Phe Thr Met Pro Glu Asp Glu Gly Val Pro Gly Gln Val Asp Ala
    50                  55                  60

Ala Met Ala Gly Arg Ile Tyr Ile Ser Gly Met Ala Pro Arg Pro Ser
65                  70                  75                  80

Leu Ala Lys Lys Gln Arg Phe Arg His Arg Asn Arg Lys Gly Tyr Arg
                85                  90                  95

Ser Gln Arg Gly His Ser Arg Gly Arg Asn Gln Asn
            100                 105

<210> SEQ ID NO 17
<211> LENGTH: 118
<212> TYPE: PRT
<213> ORGANISM: Artificial Sequence
<220> FEATURE:
<223> OTHER INFORMATION: Synthetic Peptide RCP-4

<400> SEQUENCE: 17

Met Asp Gln Glu Ser Cys Lys Gly Arg Cys Thr Glu Gly Phe Asn Val
1               5                   10                  15

Asp Lys Lys Cys Gln Cys Asp Glu Leu Cys Ser Tyr Tyr Gln Ser Cys
                20                  25                  30

Cys Thr Asp Tyr Thr Ala Glu Cys Lys Pro Gln Val Thr Arg Gly Asp
            35                  40                  45

Val Phe Thr Met Pro Glu Asp Glu Gln Pro Gln Phe Ile Ser Arg Asp
50                  55                  60

Trp His Gly Val Pro Gly Gln Val Asp Ala Ala Met Ala Gly Arg Ile
65                  70                  75                  80

Tyr Ile Ser Gly Met Ala Pro Arg Pro Ser Leu Ala Lys Lys Gln Arg
                85                  90                  95

Phe Arg His Arg Asn Arg Lys Gly Tyr Arg Ser Gln Arg Gly His Ser
            100                 105                 110

Arg Gly Arg Asn Gln Asn
        115

<210> SEQ ID NO 18
<211> LENGTH: 128
<212> TYPE: PRT
<213> ORGANISM: Artificial Sequence
<220> FEATURE:
<223> OTHER INFORMATION: Synthetic Peptide RCP-5

<400> SEQUENCE: 18

Met Asp Gln Glu Ser Cys Lys Gly Arg Cys Thr Glu Gly Phe Asn Val
1               5                   10                  15

Asp Lys Lys Cys Gln Cys Asp Glu Leu Cys Ser Tyr Tyr Gln Ser Cys
                20                  25                  30

Cys Thr Asp Tyr Thr Ala Glu Cys Lys Pro Gln Val Thr Arg Gly Asp
            35                  40                  45

Val Phe Thr Met Pro Glu Asp Glu Phe Trp Gly Arg Thr Ser Ala Gly
50                  55                  60

Thr Arg Gln Pro Gln Phe Ile Ser Arg Asp Trp His Gly Val Pro Gly
65                  70                  75                  80

Gln Val Asp Ala Ala Met Ala Gly Arg Ile Tyr Ile Ser Gly Met Ala
                85                  90                  95

Pro Arg Pro Ser Leu Ala Lys Lys Gln Arg Phe Arg His Arg Asn Arg
            100                 105                 110

Lys Gly Tyr Arg Ser Gln Arg Gly His Ser Arg Gly Arg Asn Gln Asn
        115                 120                 125

-continued

<210> SEQ ID NO 19
<211> LENGTH: 246
<212> TYPE: PRT
<213> ORGANISM: Artificial Sequence
<220> FEATURE:
<223> OTHER INFORMATION: Synthetic Peptide RCP-6

<400> SEQUENCE: 19

```
Met Asp Gln Glu Ser Cys Lys Gly Arg Cys Thr Glu Gly Phe Asn Val
1               5                   10                  15

Asp Lys Lys Cys Gln Cys Asp Glu Leu Cys Ser Tyr Tyr Gln Ser Cys
            20                  25                  30

Cys Thr Asp Tyr Thr Ala Glu Cys Lys Pro Gln Val Thr Arg Gly Asp
        35                  40                  45

Val Phe Thr Met Pro Glu Asp Glu Ser Gln Glu Glu Ser Glu Gly Ser
    50                  55                  60

Ser Leu Ser Ala Val Phe Glu His Phe Ala Met Met Gln Arg Asp Ser
65                  70                  75                  80

Trp Glu Asp Ile Phe Glu Leu Leu Phe Trp Gly Arg Thr Ser Ala Gly
                85                  90                  95

Thr Arg Gln Pro Gln Phe Ile Ser Arg Asp Trp His Gly Val Pro Gly
            100                 105                 110

Gln Val Asp Ala Ala Met Ala Gly Arg Ile Tyr Ile Ser Gly Met Ala
        115                 120                 125

Pro Arg Pro Ser Leu Ala Lys Lys Gln Arg Phe Arg His Arg Asn Arg
    130                 135                 140

Lys Gly Tyr Arg Ser Gln Arg Gly His Ser Arg Gly Arg Asn Gln Asn
145                 150                 155                 160

Ser Arg Arg Pro Ser Arg Ala Thr Trp Leu Ser Leu Phe Ser Ser Glu
                165                 170                 175

Glu Ser Asn Leu Gly Ala Asn Asn Tyr Asp Asp Tyr Arg Met Asp Trp
            180                 185                 190

Leu Val Pro Ala Thr Ser Glu Pro Ile Gln Ser Val Phe Phe Phe Ser
        195                 200                 205

Gly Asp Lys Tyr Tyr Arg Val Asn Leu Arg Thr Arg Arg Val Asp Thr
    210                 215                 220

Val Asp Pro Pro Tyr Pro Arg Ser Ile Ala Gln Tyr Trp Leu Gly Ser
225                 230                 235                 240

Pro Ala Pro Gly His Leu
                245
```

<210> SEQ ID NO 20
<211> LENGTH: 160
<212> TYPE: PRT
<213> ORGANISM: Artificial Sequence
<220> FEATURE:
<223> OTHER INFORMATION: Synthetic Peptide RCP-7

<400> SEQUENCE: 20

```
Met Asp Gln Glu Ser Cys Lys Gly Arg Cys Thr Glu Gly Phe Asn Val
1               5                   10                  15

Asp Lys Lys Cys Gln Cys Asp Glu Leu Cys Ser Tyr Tyr Gln Ser Cys
            20                  25                  30

Cys Thr Asp Tyr Thr Ala Glu Cys Lys Pro Gln Val Thr Arg Gly Asp
        35                  40                  45

Val Phe Thr Met Pro Glu Asp Glu Ser Gln Glu Glu Ser Glu Gly Ser
    50                  55                  60
```

```
Ser Leu Ser Ala Val Phe Glu His Phe Ala Met Met Gln Arg Asp Ser
 65                  70                  75                  80

Trp Glu Asp Ile Phe Glu Leu Leu Phe Trp Gly Arg Thr Ser Ala Gly
                 85                  90                  95

Thr Arg Gln Pro Gln Phe Ile Ser Arg Asp Trp His Gly Val Pro Gly
            100                 105                 110

Gln Val Asp Ala Ala Met Ala Gly Arg Ile Tyr Ile Ser Gly Met Ala
        115                 120                 125

Pro Arg Pro Ser Leu Ala Lys Lys Gln Arg Phe Arg His Arg Asn Arg
    130                 135                 140

Lys Gly Tyr Arg Ser Gln Arg Gly His Ser Arg Gly Arg Asn Gln Asn
145                 150                 155                 160
```

<210> SEQ ID NO 21
<211> LENGTH: 166
<212> TYPE: PRT
<213> ORGANISM: Artificial Sequence
<220> FEATURE:
<223> OTHER INFORMATION: Synthetic Peptide RCP-8

<400> SEQUENCE: 21

```
Met Asp Gln Glu Ser Cys Lys Gly Arg Cys Thr Glu Gly Phe Asn Val
 1               5                  10                  15

Asp Lys Lys Cys Gln Cys Asp Glu Leu Cys Ser Tyr Tyr Gln Ser Cys
                20                  25                  30

Cys Thr Asp Tyr Thr Ala Glu Cys Lys Pro Gln Val Thr Arg Gly Asp
            35                  40                  45

Val Phe Thr Met Pro Glu Asp Glu Ser Gln Glu Ser Glu Gly Ser
        50                  55                  60

Ser Leu Ser Ala Val Phe Glu His Phe Ala Met Met Gln Arg Asp Ser
 65                  70                  75                  80

Trp Glu Asp Ile Phe Glu Leu Leu Phe Trp Gly Arg Thr Ser Ala Gly
                 85                  90                  95

Thr Arg Gln Pro Gln Phe Ile Ser Arg Asp Trp His Gly Val Pro Gly
            100                 105                 110

Gln Val Asp Ala Ala Met Ala Gly Arg Ile Tyr Ile Ser Gly Met Ala
        115                 120                 125

Pro Arg Pro Ser Leu Ala Lys Lys Gln Arg Phe Arg His Arg Asn Arg
    130                 135                 140

Lys Gly Tyr Arg Ser Gln Arg Gly His Ser Arg Gly Arg Asn Gln Asn
145                 150                 155                 160

Ser Arg Arg Pro Ser Arg
                165
```

<210> SEQ ID NO 22
<211> LENGTH: 176
<212> TYPE: PRT
<213> ORGANISM: Artificial Sequence
<220> FEATURE:
<223> OTHER INFORMATION: Synthetic Peptide RCP-9

<400> SEQUENCE: 22

```
Met Asp Gln Glu Ser Cys Lys Gly Arg Cys Thr Glu Gly Phe Asn Val
 1               5                  10                  15

Asp Lys Lys Cys Gln Cys Asp Glu Leu Cys Ser Tyr Tyr Gln Ser Cys
                20                  25                  30

Cys Thr Asp Tyr Thr Ala Glu Cys Lys Pro Gln Val Thr Arg Gly Asp
            35                  40                  45
```

```
Val Phe Thr Met Pro Glu Asp Glu Ser Gln Glu Ser Glu Gly Ser
    50                  55                  60

Ser Leu Ser Ala Val Phe Glu His Phe Ala Met Met Gln Arg Asp Ser
65                  70                  75                  80

Trp Glu Asp Ile Phe Glu Leu Leu Phe Trp Gly Arg Thr Ser Ala Gly
                85                  90                  95

Thr Arg Gln Pro Gln Phe Ile Ser Arg Asp Trp His Gly Val Pro Gly
                100                 105                 110

Gln Val Asp Ala Ala Met Ala Gly Arg Ile Tyr Ile Ser Gly Met Ala
            115                 120                 125

Pro Arg Pro Ser Leu Ala Lys Lys Gln Arg Phe Arg His Arg Asn Arg
        130                 135                 140

Lys Gly Tyr Arg Ser Gln Arg Gly His Ser Arg Gly Arg Asn Gln Asn
145                 150                 155                 160

Ser Arg Arg Pro Ser Arg Ala Thr Trp Leu Ser Leu Phe Ser Ser Glu
                165                 170                 175

<210> SEQ ID NO 23
<211> LENGTH: 186
<212> TYPE: PRT
<213> ORGANISM: Artificial Sequence
<220> FEATURE:
<223> OTHER INFORMATION: Synthetic Peptide RCP-10

<400> SEQUENCE: 23

Met Asp Gln Glu Ser Cys Lys Gly Arg Cys Thr Glu Gly Phe Asn Val
1               5                   10                  15

Asp Lys Lys Cys Gln Cys Asp Glu Leu Cys Ser Tyr Tyr Gln Ser Cys
                20                  25                  30

Cys Thr Asp Tyr Thr Ala Glu Cys Lys Pro Gln Val Thr Arg Gly Asp
            35                  40                  45

Val Phe Thr Met Pro Glu Asp Glu Ser Gln Glu Ser Glu Gly Ser
    50                  55                  60

Ser Leu Ser Ala Val Phe Glu His Phe Ala Met Met Gln Arg Asp Ser
65                  70                  75                  80

Trp Glu Asp Ile Phe Glu Leu Leu Phe Trp Gly Arg Thr Ser Ala Gly
                85                  90                  95

Thr Arg Gln Pro Gln Phe Ile Ser Arg Asp Trp His Gly Val Pro Gly
                100                 105                 110

Gln Val Asp Ala Ala Met Ala Gly Arg Ile Tyr Ile Ser Gly Met Ala
            115                 120                 125

Pro Arg Pro Ser Leu Ala Lys Lys Gln Arg Phe Arg His Arg Asn Arg
        130                 135                 140

Lys Gly Tyr Arg Ser Gln Arg Gly His Ser Arg Gly Arg Asn Gln Asn
145                 150                 155                 160

Ser Arg Arg Pro Ser Arg Ala Thr Trp Leu Ser Leu Phe Ser Ser Glu
                165                 170                 175

Glu Ser Asn Leu Gly Ala Asn Asn Tyr Asp
                180                 185

<210> SEQ ID NO 24
<211> LENGTH: 463
<212> TYPE: PRT
<213> ORGANISM: Artificial Sequence
<220> FEATURE:
<223> OTHER INFORMATION: Synthetic Peptide CRP-11
```

<400> SEQUENCE: 24

```
Gly Pro Leu Gly Asp Gln Glu Ser Cys Lys Gly Arg Cys Thr Glu Gly
1               5                   10                  15

Phe Asn Val Asp Lys Lys Cys Gln Cys Asp Glu Leu Cys Ser Tyr Tyr
            20                  25                  30

Gln Ser Cys Cys Thr Asp Tyr Thr Ala Glu Cys Lys Pro Gln Val Thr
        35                  40                  45

Arg Gly Asp Val Phe Thr Met Pro Glu Asp Glu Tyr Thr Val Tyr Asp
    50                  55                  60

Asp Gly Glu Glu Lys Asn Asn Ala Thr Val His Glu Gln Val Gly Gly
65                  70                  75                  80

Pro Ser Leu Thr Ser Asp Leu Gln Ala Gln Ser Lys Gly Asn Pro Glu
                85                  90                  95

Gln Thr Pro Val Leu Lys Pro Glu Glu Ala Pro Ala Pro Glu Val
            100                 105                 110

Gly Ala Ser Lys Pro Glu Gly Ile Asp Ser Arg Pro Glu Thr Leu His
            115                 120                 125

Pro Gly Arg Pro Gln Pro Ala Glu Glu Glu Leu Cys Ser Gly Lys
    130                 135                 140

Pro Phe Asp Ala Phe Thr Asp Leu Lys Asn Gly Ser Leu Phe Ala Phe
145                 150                 155                 160

Arg Gly Gln Tyr Cys Tyr Glu Leu Asp Glu Lys Ala Val Arg Pro Gly
                165                 170                 175

Tyr Pro Lys Leu Ile Arg Asp Val Trp Gly Ile Glu Gly Pro Ile Asp
            180                 185                 190

Ala Ala Phe Thr Arg Ile Asn Cys Gln Gly Lys Thr Tyr Leu Phe Lys
            195                 200                 205

Gly Ser Gln Tyr Trp Arg Phe Glu Asp Gly Val Leu Asp Pro Asp Tyr
    210                 215                 220

Pro Arg Asn Ile Ser Asp Gly Phe Asp Gly Ile Pro Asp Asn Val Asp
225                 230                 235                 240

Ala Ala Leu Ala Leu Pro Ala His Ser Tyr Ser Gly Arg Glu Arg Val
                245                 250                 255

Tyr Phe Phe Lys Gly Lys Gln Tyr Trp Glu Tyr Gln Phe Gln His Gln
            260                 265                 270

Pro Ser Gln Glu Glu Cys Glu Gly Ser Ser Leu Ser Ala Val Phe Glu
    275                 280                 285

His Phe Ala Met Met Gln Arg Asp Ser Trp Glu Asp Ile Phe Glu Leu
    290                 295                 300

Leu Phe Trp Gly Arg Thr Ser Ala Gly Thr Arg Gln Pro Gln Phe Ile
305                 310                 315                 320

Ser Arg Asp Trp His Gly Val Pro Gly Gln Val Asp Ala Ala Met Ala
                325                 330                 335

Gly Arg Ile Tyr Ile Ser Gly Met Ala Pro Arg Pro Ser Leu Ala Lys
            340                 345                 350

Lys Gln Arg Phe Arg His Arg Asn Arg Lys Gly Tyr Arg Ser Gln Arg
        355                 360                 365

Gly His Ser Arg Gly Arg Asn Gln Asn Ser Arg Arg Pro Ser Arg Ala
    370                 375                 380

Thr Trp Leu Ser Leu Phe Ser Ser Glu Glu Ser Asn Leu Gly Ala Asn
385                 390                 395                 400

Asn Tyr Asp Asp Tyr Arg Met Asp Trp Leu Val Pro Ala Thr Cys Glu
                405                 410                 415
```

```
Pro Ile Gln Ser Val Phe Phe Ser Gly Asp Lys Tyr Tyr Arg Val
            420                 425                 430

Asn Leu Arg Thr Arg Arg Val Asp Thr Val Asp Pro Tyr Pro Arg
            435                 440                 445

Ser Ile Ala Gln Tyr Trp Leu Gly Cys Pro Ala Pro Gly His Leu
            450                 455                 460

<210> SEQ ID NO 25
<211> LENGTH: 272
<212> TYPE: PRT
<213> ORGANISM: Artificial Sequence
<220> FEATURE:
<223> OTHER INFORMATION: Synthetic Peptide RCP-12

<400> SEQUENCE: 25

Gly Pro Leu Gly Asp Gln Glu Ser Cys Lys Gly Arg Cys Thr Glu Gly
1               5                   10                  15

Phe Asn Val Asp Lys Lys Cys Gln Cys Asp Glu Leu Cys Ser Tyr Tyr
            20                  25                  30

Gln Ser Cys Cys Thr Asp Tyr Thr Ala Glu Cys Lys Pro Gln Val Thr
        35                  40                  45

Arg Gly Asp Val Phe Thr Met Pro Glu Asp Glu Tyr Thr Val Tyr Asp
    50                  55                  60

Asp Gly Glu Glu Lys Asn Asn Ala Thr Val His Glu Gln Val Gly Gly
65                  70                  75                  80

Pro Ser Leu Thr Ser Asp Leu Gln Ala Gln Ser Lys Gly Asn Pro Glu
                85                  90                  95

Gln Thr Pro Val Leu Lys Pro Glu Glu Glu Ala Pro Ala Pro Glu Val
            100                 105                 110

Gly Ala Ser Lys Pro Glu Gly Ile Asp Ser Arg Pro Glu Thr Leu His
        115                 120                 125

Pro Gly Arg Pro Gln Pro Pro Ala Glu Glu Glu Leu Cys Ser Gly Lys
    130                 135                 140

Pro Phe Asp Ala Phe Thr Asp Leu Lys Asn Gly Ser Leu Phe Ala Phe
145                 150                 155                 160

Arg Gly Gln Tyr Cys Tyr Glu Leu Asp Glu Lys Ala Val Arg Pro Gly
                165                 170                 175

Tyr Pro Lys Leu Ile Arg Asp Val Trp Gly Ile Glu Gly Pro Ile Asp
            180                 185                 190

Ala Ala Phe Thr Arg Ile Asn Cys Gln Gly Lys Thr Tyr Leu Phe Lys
        195                 200                 205

Gly Ser Gln Tyr Trp Arg Phe Glu Asp Gly Val Leu Asp Pro Asp Tyr
    210                 215                 220

Pro Arg Asn Ile Ser Asp Gly Phe Asp Gly Ile Pro Asp Asn Val Asp
225                 230                 235                 240

Ala Ala Leu Ala Leu Pro Ala His Ser Tyr Ser Gly Arg Glu Arg Val
                245                 250                 255

Tyr Phe Phe Lys Gly Lys Gln Tyr Trp Glu Tyr Gln Phe Gln His Gln
            260                 265                 270

<210> SEQ ID NO 26
<211> LENGTH: 134
<212> TYPE: PRT
<213> ORGANISM: Artificial Sequence
<220> FEATURE:
<223> OTHER INFORMATION: Synthetic Peptide RCP-13
```

<400> SEQUENCE: 26

Gly Pro Leu Gly Asp Gln Glu Ser Cys Lys Gly Arg Cys Thr Glu Gly
1               5                   10                  15

Phe Asn Val Asp Lys Lys Cys Gln Cys Asp Glu Leu Cys Ser Tyr Tyr
            20                  25                  30

Gln Ser Cys Cys Thr Asp Tyr Thr Ala Glu Cys Lys Pro Gln Val Thr
        35                  40                  45

Arg Gly Asp Val Phe Thr Met Pro Glu Asp Glu Tyr Thr Val Tyr Asp
50                  55                  60

Asp Gly Glu Glu Lys Asn Asn Ala Thr Val His Glu Gln Val Gly Gly
65                  70                  75                  80

Pro Ser Leu Thr Ser Asp Leu Gln Ala Gln Ser Lys Gly Asn Pro Glu
            85                  90                  95

Gln Thr Pro Val Leu Lys Pro Glu Glu Glu Ala Pro Ala Pro Glu Val
            100                 105                 110

Gly Ala Ser Lys Pro Glu Gly Ile Asp Ser Arg Pro Glu Thr Leu His
            115                 120                 125

Pro Gly Arg Pro Gln Pro
    130

<210> SEQ ID NO 27
<211> LENGTH: 59
<212> TYPE: PRT
<213> ORGANISM: Artificial Sequence
<220> FEATURE:
<223> OTHER INFORMATION: Synthetic Peptide RCP-14

<400> SEQUENCE: 27

Gly Pro Leu Gly Asp Gln Glu Ser Cys Lys Gly Arg Cys Thr Glu Gly
1               5                   10                  15

Phe Asn Val Asp Lys Lys Cys Gln Cys Asp Glu Leu Cys Ser Tyr Tyr
            20                  25                  30

Gln Ser Cys Cys Thr Asp Tyr Thr Ala Glu Cys Lys Pro Gln Val Thr
        35                  40                  45

Arg Gly Asp Val Phe Thr Met Pro Glu Asp Glu
50                  55

<210> SEQ ID NO 28
<211> LENGTH: 408
<212> TYPE: PRT
<213> ORGANISM: Artificial Sequence
<220> FEATURE:
<223> OTHER INFORMATION: Synthetic Peptide RCP-15

<400> SEQUENCE: 28

Gly Pro Leu Gly Tyr Thr Val Tyr Asp Asp Gly Glu Glu Lys Asn Asn
1               5                   10                  15

Ala Thr Val His Glu Gln Val Gly Gly Pro Ser Leu Thr Ser Asp Leu
            20                  25                  30

Gln Ala Gln Ser Lys Gly Asn Pro Glu Gln Thr Pro Val Leu Lys Pro
        35                  40                  45

Glu Glu Glu Ala Pro Ala Pro Glu Val Gly Ala Ser Lys Pro Glu Gly
50                  55                  60

Ile Asp Ser Arg Pro Glu Thr Leu His Pro Gly Arg Pro Gln Pro Pro
65                  70                  75                  80

Ala Glu Glu Glu Leu Cys Ser Gly Lys Pro Phe Asp Ala Phe Thr Asp
            85                  90                  95

```
Leu Lys Asn Gly Ser Leu Phe Ala Phe Arg Gly Gln Tyr Cys Tyr Glu
            100                 105                 110

Leu Asp Glu Lys Ala Val Arg Pro Gly Tyr Pro Lys Leu Ile Arg Asp
        115                 120                 125

Val Trp Gly Ile Glu Gly Pro Ile Asp Ala Ala Phe Thr Arg Ile Asn
    130                 135                 140

Cys Gln Gly Lys Thr Tyr Leu Phe Lys Gly Ser Gln Tyr Trp Arg Phe
145                 150                 155                 160

Glu Asp Gly Val Leu Asp Pro Asp Tyr Pro Arg Asn Ile Ser Asp Gly
                165                 170                 175

Phe Asp Gly Ile Pro Asp Asn Val Asp Ala Ala Leu Ala Leu Pro Ala
            180                 185                 190

His Ser Tyr Ser Gly Arg Glu Arg Val Tyr Phe Phe Lys Gly Lys Gln
        195                 200                 205

Tyr Trp Glu Tyr Gln Phe Gln His Gln Pro Ser Gln Glu Glu Cys Glu
    210                 215                 220

Gly Ser Ser Leu Ser Ala Val Phe Glu His Phe Ala Met Met Gln Arg
225                 230                 235                 240

Asp Ser Trp Glu Asp Ile Phe Glu Leu Leu Phe Trp Gly Arg Thr Ser
                245                 250                 255

Ala Gly Thr Arg Gln Pro Gln Phe Ile Ser Arg Asp Trp His Gly Val
            260                 265                 270

Pro Gly Gln Val Asp Ala Ala Met Ala Gly Arg Ile Tyr Ile Ser Gly
        275                 280                 285

Met Ala Pro Arg Pro Ser Leu Ala Lys Lys Gln Arg Phe Arg His Arg
    290                 295                 300

Asn Arg Lys Gly Tyr Arg Ser Gln Arg Gly His Ser Arg Gly Arg Asn
305                 310                 315                 320

Gln Asn Ser Arg Arg Pro Ser Arg Ala Thr Trp Leu Ser Leu Phe Ser
                325                 330                 335

Ser Glu Glu Ser Asn Leu Gly Ala Asn Asn Tyr Asp Asp Tyr Arg Met
            340                 345                 350

Asp Trp Leu Val Pro Ala Thr Cys Glu Pro Ile Gln Ser Val Phe Phe
        355                 360                 365

Phe Ser Gly Asp Lys Tyr Tyr Arg Val Asn Leu Arg Thr Arg Arg Val
    370                 375                 380

Asp Thr Val Asp Pro Pro Tyr Pro Arg Ser Ile Ala Gln Tyr Trp Leu
385                 390                 395                 400

Gly Cys Pro Ala Pro Gly His Leu
                405

<210> SEQ ID NO 29
<211> LENGTH: 195
<212> TYPE: PRT
<213> ORGANISM: Artificial Sequence
<220> FEATURE:
<223> OTHER INFORMATION: Synthetic Peptide RCP-16

<400> SEQUENCE: 29

Gly Pro Leu Gly Pro Ser Gln Glu Glu Cys Glu Gly Ser Ser Leu Ser
1               5                   10                  15

Ala Val Phe Glu His Phe Ala Met Met Gln Arg Asp Ser Trp Glu Asp
            20                  25                  30

Ile Phe Glu Leu Leu Phe Trp Gly Arg Thr Ser Ala Gly Thr Arg Gln
        35                  40                  45
```

```
Pro Gln Phe Ile Ser Arg Asp Trp His Gly Val Pro Gly Gln Val Asp
    50                  55                  60

Ala Ala Met Ala Gly Arg Ile Tyr Ile Ser Gly Met Ala Pro Arg Pro
 65                  70                  75                  80

Ser Leu Ala Lys Lys Gln Arg Phe Arg His Arg Asn Arg Lys Gly Tyr
                 85                  90                  95

Arg Ser Gln Arg Gly His Ser Arg Gly Arg Asn Gln Asn Ser Arg Arg
            100                 105                 110

Pro Ser Arg Ala Thr Trp Leu Ser Leu Phe Ser Ser Glu Glu Ser Asn
            115                 120                 125

Leu Gly Ala Asn Asn Tyr Asp Asp Tyr Arg Met Asp Trp Leu Val Pro
130                 135                 140

Ala Thr Cys Glu Pro Ile Gln Ser Val Phe Phe Ser Gly Asp Lys
145                 150                 155                 160

Tyr Tyr Arg Val Asn Leu Arg Thr Arg Val Asp Thr Val Asp Pro
                165                 170                 175

Pro Tyr Pro Arg Ser Ile Ala Gln Tyr Trp Leu Gly Cys Pro Ala Pro
            180                 185                 190

Gly His Leu
        195

<210> SEQ ID NO 30
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 30

Asp Gln Glu Ser Cys Lys Gly Arg Cys Thr Glu Gly Phe Asn Val Asp
 1               5                  10                  15

Lys Lys Cys Gln
            20

<210> SEQ ID NO 31
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 31

Lys Gly Arg Cys Thr Glu Gly Phe Asn Val Asp Lys Lys Cys Gln Cys
 1               5                  10                  15

Asp Glu Leu Cys
            20

<210> SEQ ID NO 32
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 32

Glu Gly Phe Asn Val Asp Lys Lys Cys Gln Cys Asp Glu Leu Cys Ser
 1               5                  10                  15

Tyr Tyr Gln Ser
            20
```

```
<210> SEQ ID NO 33
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 33

Asp Lys Lys Cys Gln Cys Asp Glu Leu Cys Ser Tyr Tyr Gln Ser Cys
1               5                   10                  15

Cys Thr Asp Tyr
            20

<210> SEQ ID NO 34
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 34

Cys Cys Thr Asp Tyr Thr Ala Glu Cys Lys Pro Gln Val Thr Arg Gly
1               5                   10                  15

Asp Val Phe Thr
            20

<210> SEQ ID NO 35
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 35

Thr Ala Glu Cys Lys Pro Gln Val Thr Arg Gly Asp Val Phe Thr Met
1               5                   10                  15

Pro Glu Asp Glu
            20

<210> SEQ ID NO 36
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 36

Cys Cys Thr Asp Tyr Thr Ala Glu Cys Lys Pro Gln Val Thr Arg Gly
1               5                   10                  15

Glu Val Phe Thr
            20

<210> SEQ ID NO 37
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 37

Thr Ala Glu Cys Lys Pro Gln Val Thr Arg Gly Glu Val Phe Thr Met
1               5                   10                  15

Pro Glu Asp Glu
            20
```

```
<210> SEQ ID NO 38
<211> LENGTH: 142
<212> TYPE: PRT
<213> ORGANISM: Artificial Sequence
<220> FEATURE:
<223> OTHER INFORMATION: Synthetic Peptide RCP-17aa

<400> SEQUENCE: 38

Asp Gln Glu Ser Cys Lys Gly Arg Cys Thr Glu Gly Phe Asn Val Asp
1               5                   10                  15

Lys Lys Cys Gln Cys Asp Glu Leu Cys Ser Tyr Tyr Gln Ser Cys Cys
                20                  25                  30

Thr Asp Tyr Thr Ala Glu Cys Lys Pro Gln Val Thr Arg Gly Asp Val
            35                  40                  45

Phe Thr Met Pro Glu Asp Glu Ser Gln Glu Glu Ser Glu Gly Ser Glu
        50                  55                  60

Asp Ile Phe Glu Leu Leu Phe Trp Gly Arg Thr Ser Ala Gly Thr Arg
65                  70                  75                  80

Gln Pro Gln Phe Ile Ser Arg Asp Trp His Gly Val Pro Gly Gln Val
                85                  90                  95

Asp Ala Ala Met Ala Gly Arg Ile Tyr Ile Ser Gly Met Ala Pro Arg
                100                 105                 110

Pro Ser Leu Ala Lys Lys Gln Arg Phe Arg His Arg Asn Arg Lys Gly
            115                 120                 125

Tyr Arg Ser Gln Arg Gly His Ser Arg Gly Arg Asn Gln Asn
        130                 135                 140

<210> SEQ ID NO 39
<211> LENGTH: 143
<212> TYPE: PRT
<213> ORGANISM: Artificial Sequence
<220> FEATURE:
<223> OTHER INFORMATION: Synthetic Peptide RCP-17

<400> SEQUENCE: 39

Met Asp Gln Glu Ser Cys Lys Gly Arg Cys Thr Glu Gly Phe Asn Val
1               5                   10                  15

Asp Lys Lys Cys Gln Cys Asp Glu Leu Cys Ser Tyr Tyr Gln Ser Cys
                20                  25                  30

Cys Thr Asp Tyr Thr Ala Glu Cys Lys Pro Gln Val Thr Arg Gly Asp
            35                  40                  45

Val Phe Thr Met Pro Glu Asp Glu Ser Gln Glu Glu Ser Glu Gly Ser
        50                  55                  60

Glu Asp Ile Phe Glu Leu Leu Phe Trp Gly Arg Thr Ser Ala Gly Thr
65                  70                  75                  80

Arg Gln Pro Gln Phe Ile Ser Arg Asp Trp His Gly Val Pro Gly Gln
                85                  90                  95

Val Asp Ala Ala Met Ala Gly Arg Ile Tyr Ile Ser Gly Met Ala Pro
                100                 105                 110

Arg Pro Ser Leu Ala Lys Lys Gln Arg Phe Arg His Arg Asn Arg Lys
            115                 120                 125

Gly Tyr Arg Ser Gln Arg Gly His Ser Arg Gly Arg Asn Gln Asn
        130                 135                 140

<210> SEQ ID NO 40
<211> LENGTH: 4
<212> TYPE: PRT
<213> ORGANISM: Artificial Sequence
```

```
<220> FEATURE:
<223> OTHER INFORMATION: Synthetic Peptide

<400> SEQUENCE: 40

Gly Pro Leu Gly
1

<210> SEQ ID NO 41
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 41

Gly Gly Gly Ser
1

<210> SEQ ID NO 42
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 42

Gly Gly Gly Gly Ser
1               5

<210> SEQ ID NO 43
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 43

Gly Gly Gly Gly Gly Ser
1               5
```